United States Patent
Joly et al.

(10) Patent No.: US 6,342,495 B1
(45) Date of Patent: Jan. 29, 2002

(54) AGONISTS AND ANTAGONISTS OF PERIPHERAL-TYPE BENZODIAZEPINE RECEPTORS

(75) Inventors: Alison Joly, San Mateo; George F. Schreiner, Los Altos Hills; Lawrence W. Stanton, Redwood City; R. Tyler White, Fremont, all of CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/461,780

(22) Filed: Dec. 15, 1999

Related U.S. Application Data
(60) Provisional application No. 60/113,008, filed on Dec. 18, 1998, and provisional application No. 60/136,203, filed on May 26, 1999.

(51) Int. Cl.$^7$ .......................... A61K 31/55; A61K 31/47
(52) U.S. Cl. ........................................ 514/221; 514/307
(58) Field of Search ................................. 514/307, 221

(56) References Cited

U.S. PATENT DOCUMENTS

| | | |
|---|---|---|
| 4,808,599 A | 2/1989 | Dubroeucq et al. |
| 5,026,711 A | 6/1991 | Mendes et al. |
| 5,128,338 A | 7/1992 | Bourguignon et al. |
| 5,550,124 A | 8/1996 | Gee |
| 5,776,946 A | 7/1998 | McGeer et al. |

FOREIGN PATENT DOCUMENTS

| | | |
|---|---|---|
| EP | 210084 | 1/1987 |
| EP | 248734 | 12/1987 |
| EP | 446141 | 9/1991 |
| EP | 524846 | 1/1993 |
| FR | 2669926 | 11/1990 |
| FR | 2678269 | 6/1991 |
| WO | WO 96/32383 | 10/1996 |
| WO | WO 99/58117 | 11/1999 |

OTHER PUBLICATIONS

Adinoff et al., "Vagal tone decreases following intravenous diazepam," *Psychiatry Research* 41:89–97 (1992).

DiMicco, "Evidence for control of cardiac vagal tone by benzodiazepine receptors," *Neuropharmacology* 26:553–559 (1987).

Edoute et al., "Ro 5–4864 and PK 11195, but not diazepam, depress cardiac function in an isolated working rat heart model," *Pharmacology* 46:224–230 (1993).

Grupp et al., "Benzodiazepine Ro 5–4864 increases coronary flow," *Eur. J. Pharm.* 143:143–147 (1987).

Leeuwin et al., "PK 11195 antagonizes the positive inotropic response of the isolated rat heart to diazepam but not the negative inotropic response," *Eur. J. Pharm.* 299:149–152 (1996).

Leeuwin et al., "Actions of enzodiazepines on the inotropy of the perfused rat heart," *Arch. Int. Pharmacodyn.* 326:5–12 (1993).

Shany et al., "Ro 5–4864 has a negative inotropic effect on human atrial muscle strips that is not antagonized by PK 11195," *Eur. J. Pharm.* 253:231–236 (1994).

Mestre et al., "Electrophysiological and pharmacological characterization of peripheral benzodiazepine receptors in a guinea pig heart preparation," *Life Sciences* 35:953–962 (1984).

Charbonneau et al., "Peripheral–type benzodiazepine receptors in the living heart characterized by positron emission tomography," *Circulation* 73:476–483 (1986).

Davies and Huston, "Peripheral benzodiazepine binding sites in heart and their interaction with dipyridamole," *Eur. J. Pharm.* 73:209–211 (1981).

Kruger et al., "Purification, Cloning, and Expression in a Peripheral–type Benzodiazepine Receptor," *In: GABA and Benzodiazepine Receptor Sybtypes*, Biggio and Costa eds., pp. 1–14 (1990).

Sprengel et al., "Molecular cloning and expression of cDNA encoding a peripheral–type benzodiazepine receptor," *J. Biol. Chem.* 264:20,415–20,421 (1989).

Parola et al., "Cloning and expression of a pharmacologically unique bovine peripheral–type benzodiazepine receptor isoquinoline binding protein," *J. Biol. Chem.* 266:14, 082–14,087 (1991).

Riond et al., "Molecular cloning and chroomosomal localizatin of a human periphreral–type benzodiazepine receptor," *Eur. J. Biochem.* 195:305–311 (1991).

Garnier et al., "In vitro reconstitution of a functional peripheral–type benzodiazepine receptor from mouse leydig tumor cells," *Mol. Pharmac.* 45:201–211 (1993).

Smith et al., "Comparison of biosequences," *Adv. Appl. Math.* 2:482 (1981).

Needleman et al., "A general method applicable to the search for similarities in the amino acid sequence of two proteins," *J. Mol. Biol.* 48:443 (1970).

(List continued on next page.)

*Primary Examiner*—Raymond Henley, III
(74) *Attorney, Agent, or Firm*—Knobbe, Martens, Olson & Bear, LLP

(57) ABSTRACT

The invention concerns the use of agonists and antagonists of peripheral-type benzodiazcpine receptors (PTBR) in the diagnosis and treatment of cardiac hypertrophy and other circulatory conditions. The invention specifically concerns the use of PTBR antagonists in the prevention or treatment of decompensated cardiac hypertrophy and, eventually, heart failure. The invention also concerns the use of PTBR agonists in the management of conditions calling for increased blood flow or cardiac output, including injury or functional compromise of the heart, increased demand for physical exercise, or an acquired or inherited predisposition to cardiac contractile disfunction. Pharmaceutical compositions for the treatment of such conditions and screening methods to identify PTBR agonists and antagonists are also included.

37 Claims, 13 Drawing Sheets

OTHER PUBLICATIONS

Pearson et al., "Improved tools for biological sequence comparison," *Proc. Natl. Acad. Sci. USA* 85:2444 (1988).

Altschul et al., "Gapped BLAST and PSI–BLAST: a new generation of protein database search programs," *Nulcleic Acids Res.* 25:3389–3402 (1997).

Berkovich et al., "A natural processing product of rat diazapam binding inhibitor, triakontatetraneuropeptide (diazepam binding inhibitor 17–50) contains an α–helix, which allows discrimination between benzodiazepine binding site subtypes," *Mol. Pharmac.* 37:164–172 (1990).

Guidotti., :Diazepam binding inhibitor (DBI): a peptide with multiple biological actions, *Life Sci.* 49(5):325–44 (1991).

Besman et al., "Identification of des–(Gly–lie)–endozepine as an effector of corticotropin–dependent adrenal steroidogenesis: Stimulation of cholesterol delivery is mediated by the peripheral benzodiazepine receptor," *Proc. Natl. Acad. Sci. USA* 86:4897–4901 (1989).

Taketani et al., "Involvement of peripheral–type benzodiazepine receptors in the intracellular transport of Heme and Porphyrins," *J. Biochem.* 117:875–880 (1995).

Anzini et al., "Molecular basis of peripheral vs central benzodiazepine receptor selectivity in a new class of peripheral benzodiazepine receptor ligands related to alpidem," *J. Med. Chem.* 4275 (1996).

Cappelli et al., "Mapping the peripheral benzodiazepine receptor binding site by conformationally restrained derivatives of 1–(2–Chlorophenyl)–N–methyl–N–(1–methylpropyl)–3–isoquinolinccarboxamide (PK11195)," *J. Med. Chem.* 2910 (1997.

Schoemaker et al., "Specific high–affinity binding sites for [$3^H$]Ro 5–4864 in rat brain and kidney," *J. Pharmacol. Exp. Ther.* 285:61–69 (1983).

Arola et al., "Experimental Myocarditis induced by two different coxsackievirus B3 variants: aspects of pathogenesis and comparison of diagnostic methods," *J. Med. Virol.* 47:251–259 (1995).

Chow et al., "Differential effects of myocarditic variants of coxsackievirus B3 in inbred mice, A pathologic characterization of heart tissue damage," *Lab. Invest.* 64:55–64 (1991).

McManus et al., "Direct myocardial injury by entervirus: a central role in the evolution of murine myocarditis," *Clin. Immunol. Immunopathol.* 68:159–169 (1993).

Melnick et al., "Pathogenesis of coxsackie virus infection, Multiplication of virus and evolution of the muscle lesion in mice," *J. Expert. Med.* 93:247–266 (1951).

Anderson et al., "Direct interactins of coxsackievirus B3 with immune cells in the splenic compartment of mice susceptible or resistant to myocarditis," *J. Virol.* 70:4632–4645 (1996).

Hohenadi et al., "Strand–specific detection of enteroviral RNA in myocardial tissue by in situ hybridization," *Mol. Cell. Probes* 5:11–20 (1991).

Pfeffer et al., "Influence of Chronic Captopril Therapy on the Infacted Left Ventricle of the Rat," *Circ. Res.* 57:84–95 (1985).

Bishop et al., "Three abundance classes in HeLa cell messenger RNA," *Nature* 250(463):199–204 (1974).

Leeuwin, R.S. et al., Modification of cardiac actions of RO 05–4864 by PK 11195 and flumazenil in the perfused rat heart. *Life Sciences* 61 (17):1631–42 (1997).

FIGURE 4

Expression Report

| CloneID | Name | MI Left Ventricle | | | | | MI Septum | | | | | Viral myocarditis | | | | LVH | PKD |
|---|---|---|---|---|---|---|---|---|---|---|---|---|---|---|---|---|---|
| | | 2w | 4w | 8w | 12w | 16w | 2w | 4w | 8w | 12w | 16w | 3d | 9d | 30d | 10w | |
| P0182_F08 | BTG2 | -1.9 | -1.4 | -1.6 | 1.2 | 1.0 | -2.2 | -2.4 | -1.6 | -1.0 | 1.2 | 5.4 | 2.0 | -1.5 | 1.5 | |
| P0204_E06 | 1-8U | 2.0 | 2.3 | 2.4 | 2.1 | 2.1 | 1.3 | 1.7 | 1.7 | 1.4 | 1.4 | 4.1 | 4.3 | 1.5 | -1.4 | -1.1 |
| P0207_C03 | gas-1 | 1.3 | 1.5 | 1.1 | -1.1 | 1.0 | 1.1 | 1.4 | 1.2 | 1.1 | -1.3 | -1.3 | -1.3 | -1.3 | | 1.9 |
| P0214_A11 | YMP | 1.7 | 2.4 | 1.5 | 1.9 | 1.6 | 1.3 | 1.3 | 1.3 | 1.2 | 1.0 | -1.2 | 2.0 | 1.4 | -1.4 | -1.1 |
| P0219_H09 | SDF1a | -1.0 | 1.2 | -1.1 | 1.1 | -1.0 | -1.1 | 1.3 | -1.1 | -1.1 | 1.1 | -1.3 | -1.3 | -1.0 | 2.0 | 2.4 |
| P0228_H09 | tissue specific mRNA | 1.5 | 2.2 | 1.9 | 1.9 | 1.5 | 1.4 | 1.2 | 1.3 | 1.6 | 1.3 | 2.0 | 3.0 | 1.6 | -1.2 | -1.9 |
| P0242_B03 | peripheral benzodiazepine receptor | 1.1 | 1.0 | 1.6 | 1.2 | 1.2 | 1.4 | 1.0 | 1.4 | 1.4 | 1.3 | 2.3 | 6.0 | 1.7 | -2.1 | 1.6 |
| P0246_H10 | IGFBP-6 | 2.1 | 2.4 | 2.4 | 2.7 | 2.7 | 1.1 | 1.4 | 1.5 | 1.3 | 1.5 | | 1.2 | -1.1 | 1.5 | 2.0 |
| P0248_D11 | osf-2 | 6.2 | 8.4 | 4.3 | 4.3 | 4.7 | 2.2 | 4.1 | 2.2 | 1.5 | 2.1 | -1.3 | 2.2 | 1.1 | 1.5 | 1.1 |
| P0267_B09 | OSF-1 | 1.5 | 2.1 | 1.2 | 1.3 | 1.6 | 1.3 | 1.4 | 1.3 | -1.4 | 1.0 | | 1.1 | 1.3 | | |
| P0267_E02 | prostacyclin-stimulating factor | 2.7 | 3.3 | 2.7 | 2.4 | 2.4 | 1.3 | 1.7 | 1.5 | 1.3 | 1.3 | -1.1 | 1.7 | 1.2 | 1.5 | -2.6 |
| P0268_G09 | cellular ligand of annexin II (p11) | 3.2 | 3.2 | 2.7 | 3.1 | 2.6 | 2.3 | 1.8 | 2.1 | 1.6 | 1.4 | 1.0 | 4.2 | 1.3 | -1.8 | -1.3 |
| | | | | | | | | | | | | | | | | 3.4 |

FIGURE 5

```
  5 GATCTTTCCAGAACAGCAGTTGCAATCACTATGTCTCAATCCTGGGTACC  54
    || ||  || ||||||||| ||||    | ||| | |   |||||||| ||
 32 GAGCTCCCCTGAACAGCAGCTGCAGCAGCCATGGCCCCGCCCTGGGTGCC  81

55 CGCCGTGGGCCTCACTCTGGTGCCCAGCCTGGGGGGCTTCATGGGAGCCT 104
    |||| ||||| |||| ||||  |||||||||||||| ||||| ||||  ||
 82 CGCCATGGGCTTCACGCTGGCGCCCAGCCTGGGGTGCTTCGTGGGCTCCC 131

105 ACTTTGTGCGTGGTGAGGGCCTCCGCTGGTATGCTAGCTTGCAGAAACCC 154
    ||||||  |  ||  |||||  ||||||||||||||| ||  |||||||| |||
132 GCTTTGTCCACGGCGAGGGTCTCCGCTGGTACGCCGGCCTGCAGAAGCCC 181

155 TCCTGGCATCCGCCTCGCTGGACACTCGCTCCCATCTGGGGCACACTGTA 204
    || ||||| ||||| | ||||   || |  || ||||||||||| || ||
182 TCGTGGCACCCGCCCCACTGGGTGCTGGGCCCTGTCTGGGGCACGCTCTA 231

205 TTCGGCCATGGGGTATGGCTCCTACATAATCTGGAAAGAGCTGGGAGGTT 254
    ||  |||||||||||| ||||||||| |  |||||||||||||||||||||| |
232 CTCAGCCATGGGGTACGGCTCCTACCTGGTCTGGAAAGAGCTGGGAGGCT 281

255 TCACAGAGGAGGCTATGGTTCCCTTGGGTCTCTACACTGGTCAGCTGGCT 304
    ||||||||  |||||   |||||||| ||||  ||||||||||||| ||||||||
282 TCACAGAGAAGGCTGTGGTTCCCCTGGGCCTCTACACTGGGCAGCTGGCC 331

305 CTGAACTGGGCATGGCCCCCCATCTTCTTTGGTGCCCGGCAGATGGGCTG 354
    |||||||||||||||||||||||||||||||||||||||||| || ||||||||||
332 CTGAACTGGGCATGGCCCCCCATCTTCTTTGGTGCCCGACAAATGGGCTG 381

355 GGCTTTGGTGGACCTCATGCTTGTCAGTGGGGTGGCAACCGCCACTACCC 404
    |||  |||||||| ||| ||||  |||||||||||| |||  |:||||||||||
382 GGCCTTGGTGGATCTCCTGCTGGTCAGTGGGGCGGCGGCNGCCACTACCG 431

405 TGGCTTGGCACCGAGTGAGCCCACCGGCTGCCCGCTTGCTGTATCCTTAC 454
    ||||  |||  |||   |||||||| |  |||  ||||||| ||||  || || |||
432 TGGCCTGGTACCAGGTGAGCCCGCTGGCCGCCCGCCTGCTCTACCCCTAC 481

455 CTGGCCTGGCTGGCCTTTGCCACCATGCTCAACTACTATGTATGGCGTGA 504
    ||||||||||||||||||||| || |||| ||||||||| ||||||| ||
432 CTGGCCTGGCTGGCCTTCGCGACCACACTCAACTACTGCGTATGGCGGGA 531

505 TAACTCTGGTCGGCGAGGGGGCTCCCGGCTCACAGAGTGAGGACACCTAG 554
    |||  |||   |||   |||||     ||||| ||||||||||||  | |
```

FIGURE 6

```
agtgcccttc ccggagcgtg ccctcgccgc tgagctcccc tgaacagcag ctgcagcagc   60
catggccccg ccctgggtgc ccgccatggg cttcacgctg gcgcccagcc tggggtgctt  120
cgtgggctcc cgctttgtcc acggcgaggg tctccgctgg tacgccggcc tgcagaagcc  180
ctcgtggcac ccgcccact  gggtgctggg ccctgtctgg ggcacgctct actcagccat  240
ggggtacggc tcctacctgg tctggaaaga gctgggaggc ttcacagaga aggctgtggt  300
tccctgggc  ctctacactg ggcagctggc cctgaactgg gcatggcccc ccatcttctt  360
tggtgcccga caaatgggct gggccttggt ggatctcctg ctggtcagtg gggcggcggc  420
ngccactacc gtggcctggt accaggtgag cccgctggcc gcccgcctgc tctacccta   480
cctggcctgg ctggccttcg cgaccacact caactactgc gtatggcggg acaaccatgg  540
ctggcatggg ggacggcggc tgccagagtg agtgcccggc ccaccaggga ctgcagctgc  600
accagcaggt gccatcacgc ttgtgatgtg gtggccgtca cgctttcatg accactgggc  660
ctgctagtct gtcagggcct tgcccaggg  gtcagcagag cttcagaggt tgccccacct  720
gagccccac  ccgggagcag tgtcctgtgc tttctgcatg cttagagcat gttcttggaa  780
catggaattt tataagctga ataaagtttt tgacttcctt t  821
```

FIGURE 7
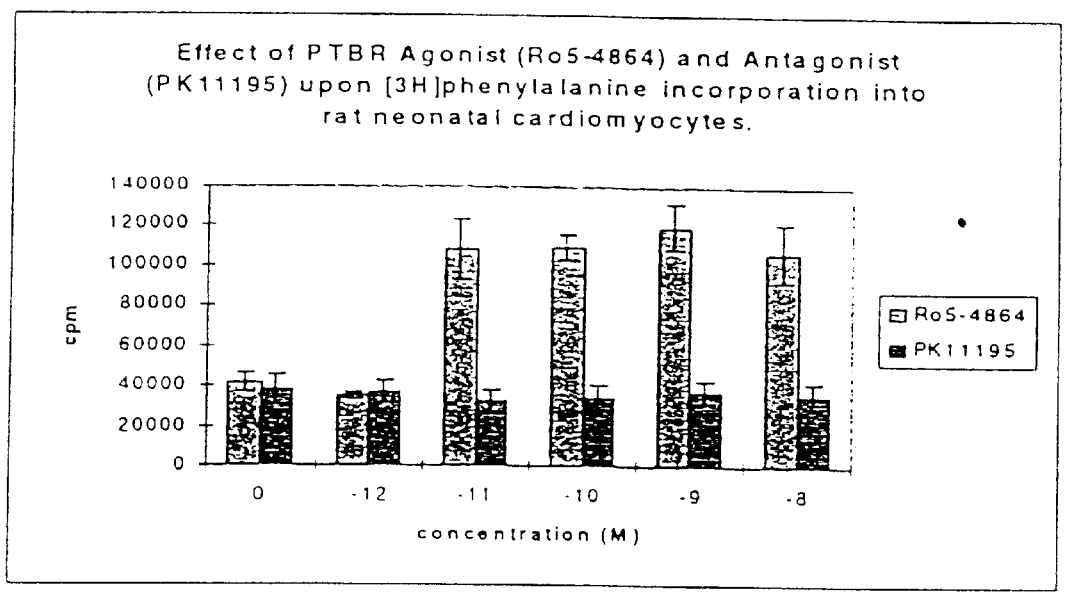
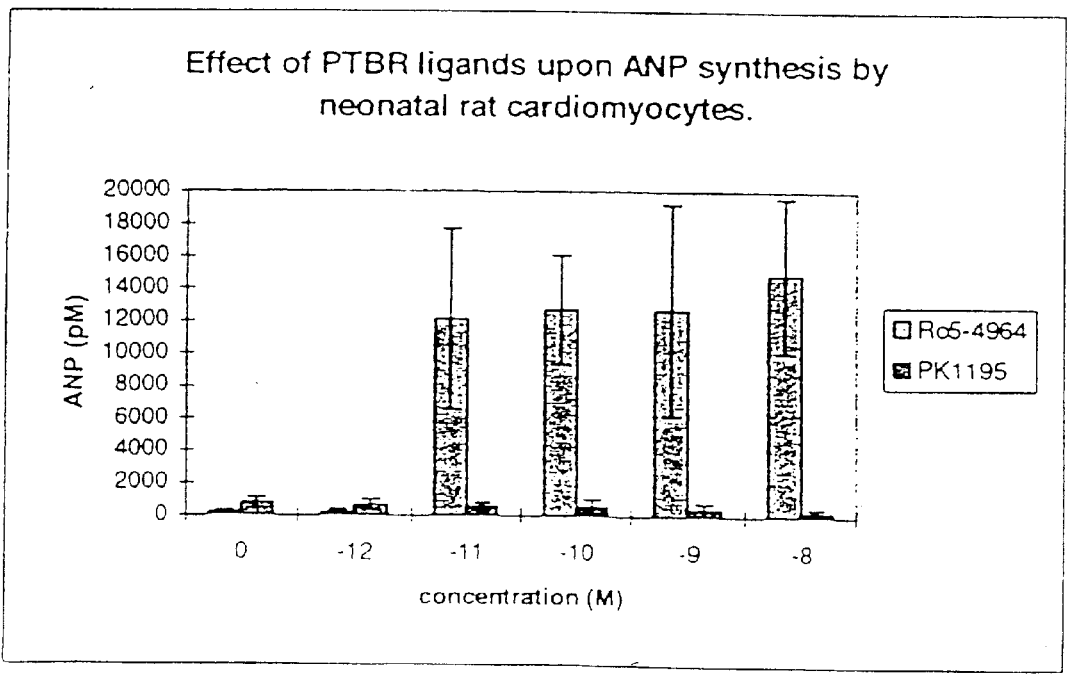

FIGURE 10A
control
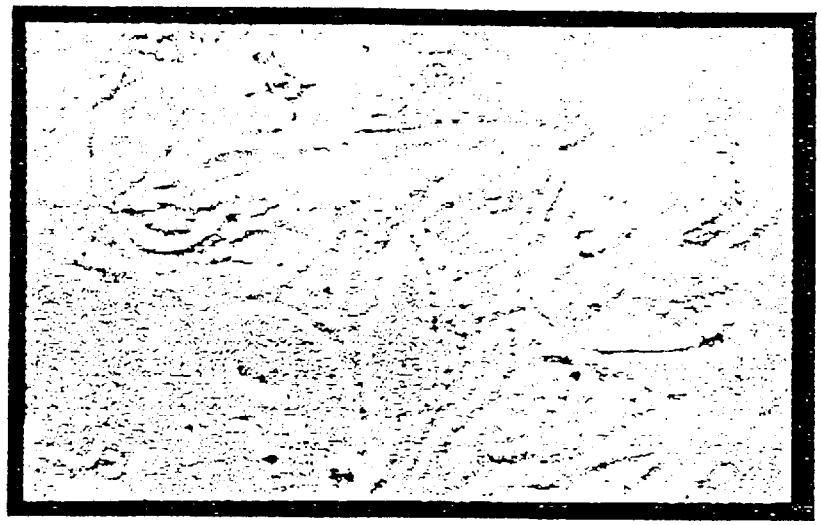
Ro5-4864
$10^{-10}$M

FIGURE 10B
control
Ro5-4864
$10^{-10}$M
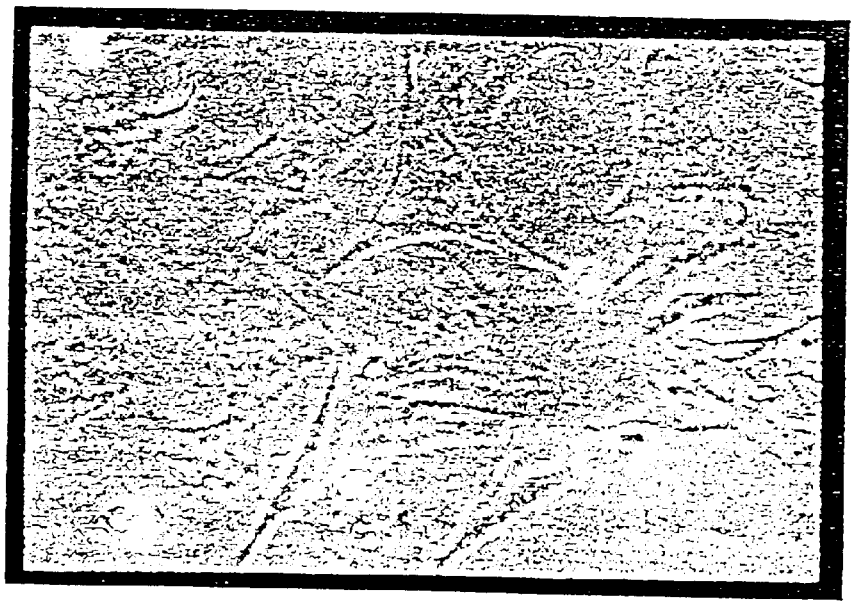

FIGURE 10C
control
Ro5-4864
$10^{-10}$M
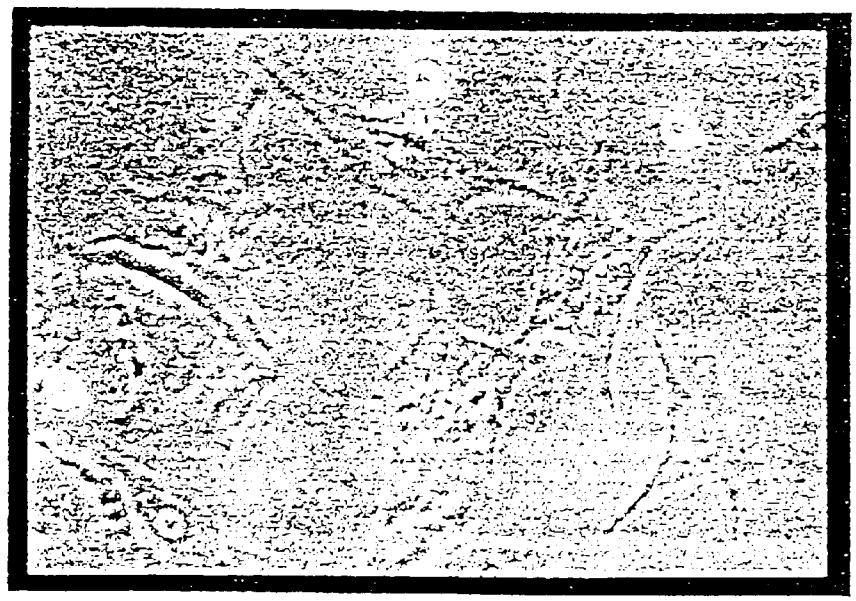

FIGURE 11
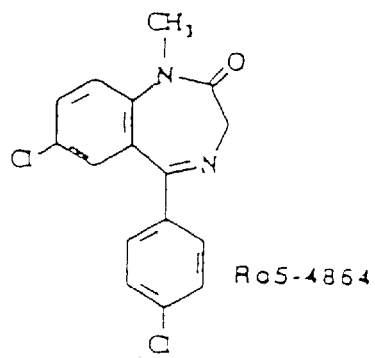
Ro5-4864
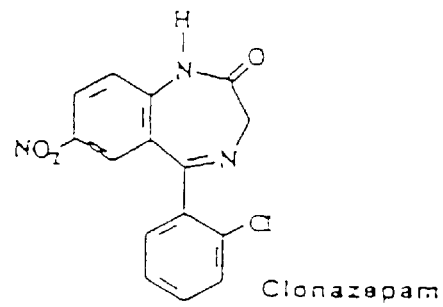
Clonazepam
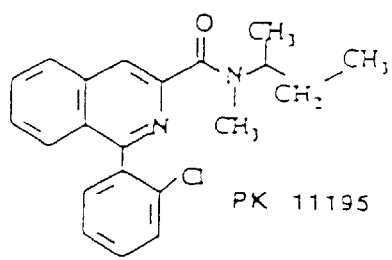
PK 11195
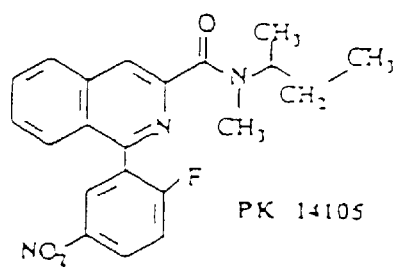
PK 14105
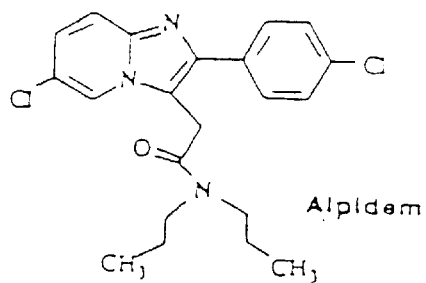
Alpidem
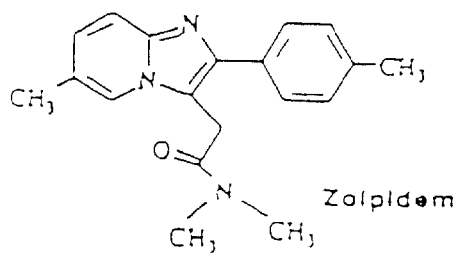
Zolpidem
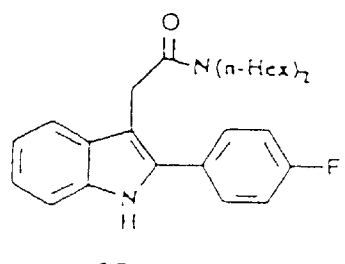
FGIN-1-27
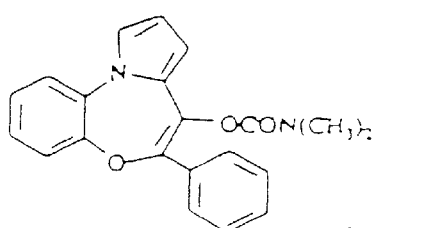
NF 182

AGONISTS AND ANTAGONISTS OF PERIPHERAL-TYPE BENZODIAZEPINE RECEPTORS

This application claims priority to U.S. Provisional Pat. application No. 60/113,008, filed Dec. 18, 1998.

FIELD OF THE INVENTION

The present invention concerns the use of agonists and antagonists of the peripheral-type benzodiazepine receptors (PTBRs). More particularly, the invention concerns the use of PTBR agonists and antagonists (including PTBR ligands) in the diagnosis and treatment of cardiac hypertrophy and other circulatory conditions.

BACKGROUND OF THE INVENTION

In response to hormonal, physiological, hemodynamic and pathological stimuli, adult ventricular muscle cells can adapt to increased workloads through the activation of a hypertrophic process. This process is characterized by an increase in the contractile protein content of cardiac muscle cells without a proliferative response because the adult cardiomyocyte is terminally differentiated and has lost its ability to divide. Cardiac growth during the hypertrophic process therefore results primarily from an increase in protein content per individual cardiomyocyte, with little or no change in cell number. The acquisition of the cardiac hypertrophic phenotype is in part dependent upon the activation of cardiac muscle gene program.

In addition to the induction of specific contractile protein components, ventricular hypertrophy is also characterized by alterations in the expression of certain non-contractile proteins, such as atrial natriuretic peptide (ANP, also known as ANF). During embryonic development, the ANP gene is expressed in both the atrium and the ventricle. However, shortly after birth ANP expression is down regulated in the ventricle and expression is mainly confined to the atrium. Following induction of hypertrophy, ANP is reexpressed in the ventriculum. Thus, ANP expression can be considered to be a non-contractile protein marker of cardiac ventricular hypertrophy.

Ventricular hypertrophy is initially a compensatory mechanism by which the heart is attempting to counteract the effects of conditions like pressure overload, loss of contractile tissue, obstruction of blood flow, or increased peripheral demand for blood flow, all of which can be generated by a variety of physiological or pathological stimuli. In some circumstances, such as, injury or functional compromise of the heart, a typically short term, compensated hypertrophic response is desirable. Similarly, cardiac, e.g. left ventricular, hypertrophy (physiological hypertrophy) is often observed in some highly trained athletes, without any apparent cardiovascular complications. However, under some circumstances the hypertrophic response may eventually contribute to cardiac dysfunction. These circumstances include, but are not limited to, excessive hypertrophy, prolonged hypertrophy, or hypertrophy occurring in the context of toxic factors or toxic concentrations of factors that, when combined with the hypertrophic response of cardiac myocytes, result in mechanical dysfunction, electrical conduction dysfunction, loss of cardiac wall elasticity, or stimulation of fibrosis. In these cases hypertrophy is termed decompensated hypertrophy, and antagonism of cardiac hypertrophy is considered desirable. Once the transition from compensated to decompensated hypertrophy is achieved, the progression to a terminal heart failure phenotype often rapidly follows.

Heart failure affects approximately five million Americans. New cases of heart failure number about 400,000 each year. The pathophysiology of congestive heart failure is rather complex. In general, congestive heart failure is a syndrome characterized by left ventricular dysfunction, reduced exercise tolerance, impaired quality of life, and markedly shortened life expectancy. Decreased contractility of the left ventricle leads to reduced cardiac output with consequent systemic arterial and venous vasoconstriction. This vasoconstriction, which promotes the vicious cycle of further reductions of stroke volume followed by an increased elevation of vascular resistance, appears to be mediated, in part, by the renin-angiotensin system. Numerous etiologies contribute to the development of CHF, including primary diseases of, or insults to, the myocardium itself, cardiac defects, hypertension, inflammation, kidney disease and vascular disease. These conditions lead to the hypertrophy and remodeling of the cardiac ventricles which, if unchecked, ultimately reduce the mechanical performance of the heart. Forces associated with the inability of the heart to pump blood ultimately lead to the release of neurohormones like catecholamines, renin-angiotensin, aldosterone, endothelin and related factors into the circulation. It has been demonstrated that elevations in plasma levels of many of these circulating neurohoiiones may have a deleterious impact on the outcome of patients with CHF. Local production of these neurohormonal factors in the heart is believed to contribute centrally to the disease. Thus, an important therapeutic strategy has been to block this neurohormonal axis contributing to the pathogenesis of this disease.

Factors known to contribute centrally to the pathophysiology of heart disease are biosynthesized in the heart itself. These factors are produced in cardiac myocytes, fibroblasts, smooth muscle and endothelial cells, and inflammatory cells associated with the myocardium. For example, the heart has been shown to contain its own renin-angiotensin system. Blockade of the cardiac renin-angiotensin system is believed to contribute significantly to the therapeutic efficacy of the therapeutic class of agents known as angiotensin converting enzyme (ACE) inhibitors.

The heart also produces other factors including, but not limited to, endothelins, bradykinin, adrenomedullin, tumor necrosis factor, transforming growth factors, and natriuretic peptides. While there are successful therapeutic approaches based on the modulation of these secondary factors, there is a need for devising different strategies that directly modulate the cardiac hypertrophic response.

Thus, there is a great interest in trying to understand the mechanisms that induce and control ventricular hypertrophy and indeed to dissect the transition from compensated to decompensated hypertrophy. There are several physiological stimuli that will induce a hypertrophic response in isolated cardiomyocytes such as endothelin-1, TGF-β and angiotensin II. Additionally, the α adrenergic agonist phenylephrine is a well-characterized and potent inducer of hypertrophy in isolated cardiomyocytes.

In the course of our functional genomic studies, the gene of a peripheral-type benzodiazepine receptor (PTBR) was found to be differentially expressed in the hearts of several rat models of heart failure. Peripheral-type benzodiazepine receptors represent a subset of the benzodiazcpine receptor family distinguished by their location outside the central nervous system (CNS). A review of PTBR's, including the molecular structure, biological properties and possible physiological roles has been published by Zisterer and Williams, *Gen. Pharmac.* 29:305–314 (1997), the entire disclosure of which is hereby expressly incorporated by reference.

Ligands of PTBR's have been known for many years and anti-depressant CNS effects of PTBR agonists (e.g. Valium) are widely known. Vagal tone has been found to decrease following intravenous administration of diazepam (Adinoff et al., *Psychiatry Research* 41:89–97 [1992]). There is evidence for control of cardiac vagal tone by benzodiazcpine receptors (DiMicco, *Neurophaimacology* 26:553–559 [1987]). PTBR ligands Ro5-4864 and PK11195, but not diazepam, have been described to depress cardiac function in an isolated working rat heart model (Edoute et al., *Pharmacology* 46:224–230 [1993]). Ro5-4864 has also been reported to increase coronary flow in an isolated perfused Langendorf rat heart without affecting heart rate and left ventricular contractility. PK11195 did not antagonize this vasodilatory effect (Grupp et al., *Eur. J. Pharm.* 143:143–147 [1987]). In an isolated rat heart preparation, diazepam induced a transient negative inotropic effect followed by a positive inotropic response. The positive inotropy was antagonized by PK11195. (Leeuwin et al., *Eur. J. Pharm.* 299:149–152 [1996]). Diazepam increased contractile force in Langendorf rat heart (Leeuwin et al., *Arch. Int. Pharmacodyn.* 326:5–12 [1993]). Ro5-4864 has been shown to have a small (20%) depressant effect on the contraction amplitude (negative inotropic effect) of human atrial strips that was not antagonized by K11195 (Shany et al., *EurJ. Pharm.* 253:231–236 [1994]). In a guinea pig heart preparation Ro5-4864 decreased the duration of intracellular action potential and contractility. Diazepam was less effective and clonazepam ineffective. The effects of Ro5-4864 were reversed by PK11195 but not by a specific antagonist of the CNS BZR. (Mestre et al., *Life Sciences* 35:953–962 [1984]). The presence of PTBR binding sites in the hearts of dogs and humans was demonstrated in vivo by positron emission tomography using [$^{11}$C]-PK11195. (Charmonneau ie al., *Circulation* 73:476–483 [1986]). It has also been reported that Ro5-4862 and dipyridamole can compete [$^3$H] diazepam binding to heart tissue. Diazepam potentiates the actions of adenosine on isolated cardiac and smooth muscle and the coronary vasodilator action of adenosine in dogs. There is evidence that diazepam may be acting in a similar manner to dipyridamole by inhibiting adenosine uptake (Davies and Huston, *Eur. J. Pharm.* 73:209–211 [1981]).

While there are reports of various effects of diazepam and its derivatives upon heart function, these effects have been attributed to their anti-depressant effects in decreasing vagal tone and not by direct effects upon cardiomyocyte function.

There is a need for the identification of endogenous and exogenous factors that will promote or inhibit the ventricular hypertrophic phenotype. Specifically, there is a need to identify factors that are therapeutics or instrumental in the identification of therapeutics effective in the treatment of heart failure or as preventative agents for the treatment of patients at high risk of developing heart failure.

SUMMARY OF THE INVENTION

The present invention concerns the use of agonist and antagonists of the peripheral-type benzodiazepine receptors (PTBR's), such as PTBR ligands, to induce or inhibit cardiac hypertrophy. In particular, the invention concerns the use of antagonists of the PTBR's in the prevention or treatment of decompensated cardiac hypertrophy and eventually, heart failure. The invention also concerns the use of agonists of the PTBR's in the management of conditions calling for increased blood flow or cardiac output, including, without limitation, injury or functional compromise of the heart, increased demand for physical exercise by athletes or by those who need extra help to improve cardiac performance as a result of a disability, existing atrio-ventricular (A–V) shunts, an acquired or inherited predisposition to cardiac contractile protein dysfunction, etc.

In one aspect, the invention concerns a method of inducing a hypertrophic response in cardiac myocytes by contacting the myocytes with an effective amount of an agonist of a peripheral-type benzodiazepine receptor (PTBR). The treatment may be performed in vitro or in vivo, and the PTBR preferably is a native receptor of a mammalian species, e.g. human, while the agonist preferably is a PTBR ligand.

In another aspect, the invention concerns a method of reducing a hypertrophic response of cardiac myocytes by contacting the myocytes with an effective amount of an antagonist of a peripheral-type benzodiazepine receptor (PTBR). Again, the treatment may be performed in vitro or in vivo, and the PTBR preferably is a native receptor of a mammalian species, e.g. human, while the antagonist preferably is a PTBR ligand.

In yet another aspect, the invention concerns a method for the treatment (including prevention) of cardiac hypertrophy by administering to a patient an effective amount of a PTBR antagonist. The cardiac hypertrophy to be treated preferably is decompensated hypertrophy, and the preferred treatment is early intervention used to prevent, reverse, or slow down the progression of this condition.

In a further aspect, the invention concerns a method for inducing compensated cardiac hypertrophy by administering to a patient in need an effective amount of a PTBR agonist. This approach is typically used in a situation where increased blood flow or pressure would be beneficial without fear of adverse consequences, such as congestive heart failure or decompensation. Hence, PTBR agonists are particularly useful in the treatment (including prevention) of conditions where a, typically short term, compensatory mechanism is desirable to respond to factors like pressure overload, loss of contractile tissue or function, obstruction of blood flow, or increased peripheral demand for blood flow or cardiac output.

In a still further aspect, the invention concerns a method of screening for a PTBR antagonist by contacting a cardiac myocyte of hypertrophic phenotype with a candidate molecule, and monitoring the reduction in hypertrophy.

In another aspect, the invention concerns a method for screening for a PTBR agonist by contacting a normal cardiac myocyte with a candidate molecule, and monitoring the appearance of hypertrophic phenotype.

In all screening assays, the candidate preferably is a molecule capable of binding to a PTBR or, in the case of PTBR antagonist candidates, to a native PTBR ligand.

In a different aspect, the invention concerns a method for the prevention of decompensated cardiac hypertrophy by administering to a patient an effective amount of a PTBR antagonist. In a preferred embodiment, the method concerns the prevention of the progression of compensated cardiac hypertrophy into decompensated cardiac hypertrophy.

In another aspect, the invention concerns a method for the treatment (including prevention) of heart failure comprising administering to a patient an effective amount of a PTBR antagonist. The heart failure may be congestive heart failure due to ischemia, drug or toxin exposure, infection, altered metabolism, genetic predisposition to altered contractile function, or other cause.

The invention further concerns a composition for the treatment (including prevention) of a cardiac disease comprising an effective amount of a PTBR antagonist or agonist, in admixture with a pharmaceutically acceptable excipient. If the composition comprises a PTBR antagonist, the cardiac disease preferably is cardiac hypertrophy regardless of the underlying mechanism. If the composition comprises a PTBR agonist, the goal preferably is to assist the patient to whom the composition is administered, in coping with a condition that calls for increased cardiac or peripheral blood flow, by inducing, under controlled conditions, compensated cardiac hypertrophy.

In yet another aspect, the invention concerns a method for diagnosing a heart disease comprising detecting an alteration in the expression level of a PTBR or an endogenous ligand thereof. The heart disease preferably is compensated or decompensated cardiac hypertrophy. Proper and timely diagnosis will enable the attending physician to customize therapeutic modalties to a patient's cardiac disease.

In a further aspect, the invention concerns a method of treating a patient in need by administering an agonist of a PTBR followed by the administration of an antagonist of a PTBR. This method is particularly useful when initially the patient is in need of increased cardiac or peripheral blood flow, for example as a result of loss of contractile tissue or obstruction of blood flow, therefore, the administration of a PTBR agonist is desirable, but later develops or is in danger of developing decompensated cardiac hypertrophy.

In all aspects, the PTBR agonist may, for example, be a native sequence PTBR ligand or a fragment or functional subunit thereof, an organic small molecule or peptide, a polypeptide variant of a native sequence ligand, an antibody, a glycopeptide, a glycolipid, a polysaccharide, an oligosaccharide, a nucleic acid, a peptidomimetic, a pharmacological agent or a metabolite thereof, a transcriptional or translational control sequence, and the like. Similarly, the PTBR antagonist may be a polypeptide, an organic small molecule or peptide, a polypeptide variant of a native sequence ligand, an antibody, a glycopeptide, a glycolipid, a polysaccharide, an oligosaccharide, a nucleic acid, a peptidomimetic, a pharmacological agent or a metabolite thereof, a transcriptional or translational control sequence, and the like. For example, PTBR antagonists include polypeptide variants of a native sequence PTBR ligand, variants of a native sequence PTBR that retain the ability to bind an endogenous ligand but are deficient in their ability to mediate biological activity, anti-PTBR or anti-PTBR ligand antibodies, and selective inhibitors of the in vivo production of an endogenous PTBR ligand. The organic small molecules are preferably selected from the chemical classes of benzodiazepines, isoquinoline carboxamides, imidazopyridines, 2-aryl-3-indoleacetamides, and pyrolobenzoxazepines. A particularly preferred agonist is Ro5-4864, while a particularly preferred antagonist is PK11195.

The PTBR agonist or antagonists may be administered orally, by intravenous or subcutaneous administration, or by direct infusion into the coronary vasculature, pericardial space, or cardiac tissue, on an acute or chronic or recurring basis.

BRIEF DESCRIPTION OF THE FIGURES

FIG. 4 shows the differential expression data of representative genes obtained through the disease models of the present invention and determined via microarray analysis. Those representative disease model differentially expressed genes (clone ID nos. P0204_E06, P0237_E02, P0248_D11, P0228_$_H$09, P0246_H10, P0237_B09, P0207_$C_{03,}$ P0214_A11, P0182_F08, P0219_H09, P0242—B03, P0268_G09) were found to correspond to human genes encoding 1-8U, prostacyclin-stimulating factor, osf-2, tissue specific mRNA, insulin-like growth factor binding protein 6, OSF-1, gas-1, YMP, BTG2, pre-B cell stimulating factor homolog (SDF1a), peripheral-type benzodiazepine receptor (PTBR), and cellular ligand of annexin II (p11), respectively.

FIG. 5 shows alignment data comparing the cDNA encoding the differentially expressed rat peripheral-type bezodiazepine receptor (P0268) gene with human cDNA corresponding to PTBR (SEQ ID NOs: 1 and 2).

FIG. 6 shows the amino acid sequence of human PTBR (SEQ ID NO:3).

FIG. 7 shows the effect of PTBR antagonist PK11195 and PTBR agonist Ro5-4864 on protein synthesis and ANP synthesis in neonatal rat cardiomyocytes.

FIG. 11 shows a representative photograph of the control and treated cultures following 24 hours of culture. FIGS. 10B and 10C show the same cultures following 96 hours of culture.

FIG. 11 shows the chemical structure of selected PTBR ligands, including PTBR agonist Ro5-4864, and antagonist PK11195.

DETAILED DESCRIPTION OF THE INVENTION

I. Definitions

Figure 1:
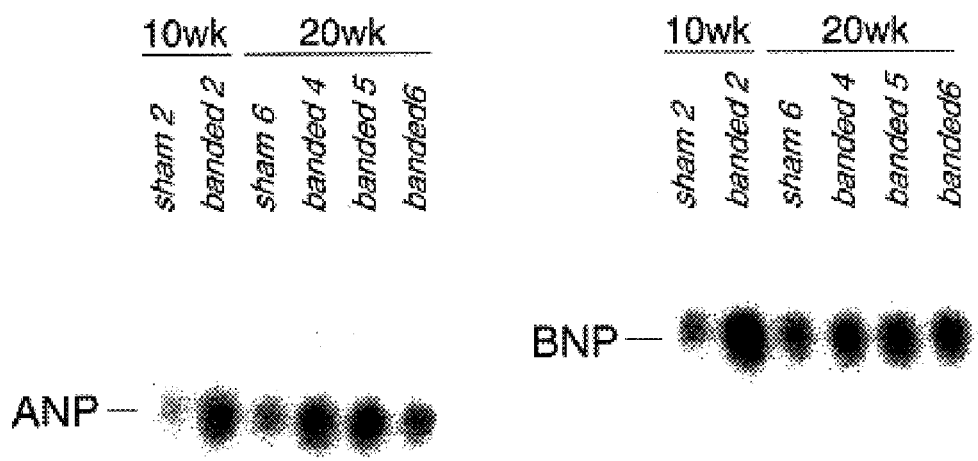
FIG. 1 shows RNA blot analysis of ANP and BNP in LVH rats. Aortic banded and sham operated control rats were sacrificed at 10 weeks and 20 weeks post surgery. RNA was extracted from the left ventricle of each animal and probed on Northern blots for ANP and BNP transcripts using specific oligonucleotide probes.

Unless defined otherwise, technical and scientific tens used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and March, *Advanced Organic Chemistry Reactions, Mechanism and Structure* 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "peripheral-type benzodiazepine receptor", "PTBR", and "PTBR polypeptide", whether used in singular or plural, are used interchangeably, and encompass any native sequence PTBR polypeptide. Such PTBR polypeptides can be isolated from a variety of sources, such as from a variety of human or non-human tissue types, or prepared by recombinant and/or synthetic methods. All such polypeptides are specifically within the scope of the definition, regardless of their mode of preparation, and include variants thereof. Thus, the terms "peripheral-type benzodiazepine receptor", "PTBR", and "PTBR polypeptide", whether used in singular or plural, refer to receptor polypeptides which bind to benzodiazepine molecules but are distinct from those associates with the central-type benzodiazepine receptors, and which have the same amino acid sequence as a respective polypeptide derived from nature. Such PTBR polypeptides can be isolated from nature or can be produced by recombinant and/or synthetic means. The term "PTBR" specifically encompasses naturally-occurring truncated or secreted forms (e.g., an extracellular domain sequence), as well as naturally occurring variant forms (e.g., alternatively spliced forms), and naturally occurring allelic variants. PTBR's represent a subset of the benzodiazepine receptor family that is located outside the central nervous system. Kruger et al., in: *GABA and Benzodiazepine Receptor Subtypes,* Biggio and Costa eds., pp. 1–14 (1990) reported the purification, cloning and expression of a peripheral-type benzodiazepine receptor. The cDNA of a 18-kDa PTBR polypeptide, originally identified in heart tissue, has subsequently been cloned from various sources, such as rat adrenal (Sprengel et al., *J. Biol. Chem.* 264:20,415–20,421 [1989]); bovine adrenal (Parola et al., *J. Biol. Chem.* 266:14, 082–14,087 [1991]); a human lymphoma cell line (Riond et al., *Eur. J. Biochem.* 195:305–311 [1991]); and a mouse Leydig tumor cell line (Garnier et al., *Mol. Pharmac.* 45:201–211 [1993]). This 169 amino acids protein has approximately 80% homology between species. Various cells transfected with these cDNAs displayed binding characteristics for PTBR ligands Ro5-4864 and PK11195. It has been suggested that PTBR is a multimeric complex in which the PK11195 binding site is on the 18-kDA subunit, and expression of the benzodiazepine binding requires another subunit, designated VDAC. Another, 10-kDa protein, associated with PTBR, has also been tentatively identified as a further component of the PTBR complex. (See, e.g. Zisterer and Williams, supra.) All of these polypeptides, alone, or in any functional combination, are specifically within the definition of "PTBR". In a particular embodiment, the peripheral-type benzodiazepine receptor has the amino acid sequence of human PTBR (SEQ ID NO: 3).

The terms "ligand" "PTBR ligand" and "ligand of a (native sequence) PTBR" are interchangeable, and are used in the broadest sense to include endogenous or exogenous factors that interact with a PTBR, including native sequence PTBR ligands and their variants, as well as synthetic, and may, but does not need to, involve specific binding to the native sequence PTBR. The term "PTBR ligand" includes antagonists and agonists, as defined below.

The terms "native sequence ligand", "native sequence PTBR ligand", "native sequence ligand of a PTBR", and grammatical equivalents thereof, are used interchangeably, and refer to endogenous ligands of a PTBR, known or hereinafter defined. Such native sequence polypeptides can be isolated from nature or can be produced by recombinant and/or synthetic means. The term "native sequence" in conjunction with the designation of a particular polypeptide specifically encompasses naturally-occurring truncated or secreted forms (e.g., an extracellular domain sequence), as well as naturally occurring variant forms (e.g., alternatively spliced forms), and naturally occurring allelic variants of the named polypeptide.

The term "antagonist" is used in the broadest sense and includes any molecule that partially or fully blocks, inhibits or neutralizes a biological activity mediated by a PTBR through preventing the binding of an agonist to the PTBR, thereby blocking the biological activity of the agonist mediated by the PTBR. In a similar manner, the term "agonist" is used in the broadest sense and includes any molecule that mimics a biological activity mediated by a PTBR, and specifically changes the function or expression of a PTBR, or the efficiency of signalling through a PTBR, thereby altering (increasing or inhibiting) an already existing biological activity or triggering a new biological activity.

The terms "variant" and "amino acid sequence variant" are used interchangeably and designate polypeptides in which one or more amino acids are added and/or substituted and/or deleted and/or inserted at the N- or C-terminus or anywhere within the corresponding native sequence, and which retain at least one activity (as defined below) of the corresponding native polypeptide. In various embodiments, a "variant" polypeptide usually has at least about 75% amino acid sequence identity, or at least about 80% amino acid sequence identity, preferably at least about 85% amino acid sequence identity, even more preferably at least about 90% amino acid sequence identity, and most preferably at least about 95% amino acid sequence identity with the amino acid sequence of the corresponding native sequence polypeptide.

"Sequence identity", is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity.

The local homology algorithm of Smith and Waterman (Smith et al., *Adv. Appl. Math.* 2:482 (1981)) can conduct optimal alignment of sequences for comparison, e.g., by the homology alignment algorithm of Needleman and Wunsch (Needleman et al., *J. Mol. Biol.* 48:443 (1970)), by the search for similarity method of Pearson and Lipman (Pearson et al., *Proc. Natl. Acad. Sci.* USA 85:2444 (1988)), by computerized implementations of these algorithms (GAP, BESTFIT, FASTA, and TFASTA in the Wisconsin Genetics Software Package, Genetics Computer Group, 575 Science Dr., Madison, Wis., or by inspection.

In a preferred embodiment, the homology alignment algorithms employed in the BLAST program (Altschul et al., *Nucleic Acids Res.* 25:3389–3402 (1997)) may be used. The BLAST family of programs allows all combinations of DNA or protein query sequences with searches against DNA or protein databases. Within the context of the present invention, the specific BLAST programs that may be utilized include: blastp, which compares an amino acid query sequence against a protein sequence database; blastn, which compares a nucleotide query sequence against a nucleotide sequence database; blastx, which compares the six-frame conceptual translation products of a nucleotide query sequences (both strands) against a protein sequence database; tblastn, which compares a protein query sequence against a nucleotide sequence database dynamically translated in all six reading frames (both strands); and tblastx, which compares the six-frame translations of a nucleotide query sequence against the six-frame translations of a nucleotide sequence database. For the blastn program, the following parameters and their default values are utilized: -G: cost to open a gap, default=5; -E: cost to extend a gap, default=2; -q: penalty for a mismatch in the blast portion of run, default=−3; -r: reward for a match in the blast portion of run, default=1; -e: expectation value (E), default =10.0; -W: word size, default is 11 for blastn, 3 for other programs; -v number of one-line descriptions (V), default=100; and -b: number of alignments to show (B), default=100.

Most preferably, the % sequence identity values are generated by the NCBI BLAST2.0 software as defined by Altschul et al., (1997), "Gapped BLAST and PSIBLAST: a new generation of protein database search programs", Nucleic Acids Res., 25:3389–3402. The parameters are set to default values, with the exception of the Penalty for mismatch, which is set to −1.

"Active" or "activity" means a qualitative biological and/or immunological property. In the context of the present invention, a preferred biological activity of an antagonist is the ability to reduce in vitro the hypertrophy shown by cardiac myocytes in response to treatment with an agonist. Even more preferably, an antagonist is biologically active, if it is capable of in vivo treatment (including prevention) of a cardiac disease, e.g. cardiac hypertrophy. A preferred agonist of the present invention will have the ability to induce cardiac hypertrophy in vitro, and/or compensated cardiac hypertrophy in vivo.

The phrase "immunological property" means immunological cross-reactivity with at least one epitope of the reference (native sequence) polypeptide molecule, wherein, "immunological cross-reactivity" means that the candidate polypeptide is capable of competitively inhibiting the qualitative biological activity of the reference (native sequence) polypeptide. The immunological cross-reactivity is preferably "specific", which means that the binding affinity of the immunologically cross-reactive molecule identified to the corresponding polypeptide is significantly higher (preferably at least about 2-times, more preferably at least about 4-times, most preferably at least about 6-times higher) than the binding affinity of that molecule to any other known native polypeptide.

"Cardiac disease" includes congestive heart failure, myocarditis, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, acute or chronic ischemic heart disease, and cardiac tumors, inherited genes or traits that dispose or predispose to altered contractile function, alone or in combination with other injury or stimuli, along with any disease or disorder that relates to the cardiovascular system and related disorders, as well as symptoms indicative of, or related to, cardiac disease and related disorders.

As used herein, "h16heart failure" refers to an abnormality of cardiac function where the heart does not pump blood at the rate needed for the requirements of metabolizing tissues. The heart failure can be caused by any number of factors, including ischemic, congenital, rheumatic, or idiopathic forms.

As used herein "congestive heart failure" refers to a syndrome characterized by left ventricular dysfunction, reduced exercise tolerance, impaired quality of life, and markedly shortened life expectancy. Decreased contractility of the left ventricle leads to reduced cardiac output with consequent systemic arterial and venous vasoconstriction. This vasoconstriction, which appears to be mediated, in part, by the renin-angiotensin system, promotes the vicious cycle of further reductions of stroke volume followed by an increased elevation of vascular resistance.

As used herein "infarct" refers to an area of necrosis resulting from an insufficiency of blood supply. "Myocardial infarction" refers to myocardial necrosis resulting from the insufficiency of coronary blood supply.

The terms "treat" or "treatment" refer to both therapeutic treatment and prophylactic or preventative measures, wherein the object is to prevent or slow down (lessen) an undesired physiological change or disorder, such as the development of cardiac hypertrophy, the transition from compensated hypertrophy to uncompensated hypertrophy, etc. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. If the condition to be treated is hypertrophy, it may be from any cause, including idiopathic, cardiotrophic, or myotrophic causes, inherited causes, or as a result of ischemia or ischemic insults such as myocardial infarction. Typically, the treatment is performed to stop or slow the progression of hypertrophy, especially after heart damage, such as from ischemia, has occurred. Preferably, for treatment of myocardial infarctions, the agent(s) is given immediately after the myocardial infarction, to prevent or lessen the injury. In the objective is to induce compensated hypertrophy, the treatment is typically relatively short term, and the appearance and progression of hypertrophy is carefully monitored. "Treatment" includes treatment regimens that include the administration of both agonists and antagonists at various stages of the disease or conditions to be treated, as well as combination treatment with the PTBR agonists and/or antagonists of the present invention and other therapeutics.

"Chronic" administration refers to administration of the agent(s) in a continuous mode as opposed to an acute mode, so as to maintain the desired, e.g. initial anti-hypertrophic, effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

An "effective amount" is an amount sufficient to effect beneficial or desired clinical results. An effective amount can be administered in one or more administrations. For purposes of this invention, an effective amount of a PTBR agonist or antagonist (including PTBR ligands) is an amount that is sufficient to effect the desired treatment, as hereinabove defined.

The term "recombinant" when used with reference to a cell, animal, or virus indicates that the cell, animal, or virus encodes a foreign DNA or RNA. For example, recombinant cells optionally express nucleic acids (e.g., RNA) not found within the native (non-recombinant) form of the cell.

The term "antibody" is used in the broadest sense and specifically covers anti-PTBR and anti-PTBR ligand monoclonal antibodies (including agonist, antagonist, and neutralizing antibodies), polyclonal antibodies, multi-specific antibodies (e.g., bispecific antibodies), as well as antibody fragments. The monoclonal antibodies specifically includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851–6855 (1984)). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); and Reichmann et al., *Nature*, 332:323–329 (1988). The humanized antibody includes a PRIMATIZED® antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057–1062 (1995)); single-chain antibody molecules; and multispecific antibodies formed from antibody fragments.

II. Modes of Carrying Out the Invention

A. Ligands of PTBR

There are several native polypeptides that have been putatively identified as endogenous ligands for PTBR or as components of such ligands. One possible endogenous ligand is the diazepam-binding inhibitor (DBI) (Berkovich et al., *Mol. Pharmac.* 37:164–172 [1990]; Guidotti et al., *Nature* 257:533–535 [1978]), an endogenous 11-kDa polypeptide of 86 amino acids (Besman et al., *Proc. Natl. Acad. Sci. USA* 86:4897–4901 [1989]). The same ligand is also referred to in the literature as acyl coenzyme A-binding protein (Knudscn et al., *Biochem. J.* 26:513–519 [1989]). This ligand is not selective as it has the same affinity ($\mu$M range) for both the GABA$_A$/benzodiazepine receptor and PTBR. A shorter fragment of DBI (fragment 17–50, also referred to as trikontetraneuropeptide) is more selective for PTBR.

Another set of putative endogenous ligands are naturally occurring porphyrins which have been reported to have high affinity for the PTBR. (Taketani et al., *J. Biochem.* 117:875–880 [1995] and Zisterer and Williams, supra.)

Synthetic ligands of the PTBR are also known and well characterized. Such synthetic ligands include benzodiazepines, such as, for example, Ro5-4864 and Clonazepam; isoquinoline carboxamides, e.g. PK 11195 [1-(2-chlorophenyl)-N-methyl-N-(1-methylpropyl)-3-isoquinoline carboxamide] and PK 14105 [(2-fluoro-5-nitrophenyl)-N-methyl-N-(1-methylpropyl)-3-isoquinoline carboxamide]; imidazopuridines, e.g. Alpidem and Zolpidem; and 2-amyl-3-indoleacetamides, e.g. FGIN-1-27; and pyrolobenoxapines, e.g. NF 182. The chemical structures of some selected synthetic PTBR ligands are shown in FIG. 11. Further synthetic PTBR ligands are also well known in the art, and are discussed, for example, in Zister and Williams, supra; Anzini et al., *J. Med. Chem.* 4275–84 (1996); Cappelli et al., *J. Med. Chem.* 2910–21 (1997) (conformationally constrained analogues of Ro5-4864); WO 96/32383 [(2-phenylpyrimidin-4-yl) (oxy or amino) acetamide derivatives]; FR 2,678,269 [1-(1-(4-chlorophenyl)-2-(1-piperidinyl)ethanol derivatives]; EP 524,846 [2-(1-piperidinyl)-2-(6(3,4-quinolin-2-(1H)-one))-ethanol derivatives]; FR 2,669,926 (phenylurea derivatives); U.S. Pat. No. 5,128,338 and EP 446,141 [imidazo(1,2-c) quinazoline derivatives]; U.S. Pat. No. 5,026,711 (4-substituted amino-quinoline or naphtyridine-3-carboxylic acid derivatives); U.S. 4,808,599 and EP 248,734 (benzothiphene or benzofuran carboxamide derivatives); and EP 210,084 (amide or carbamate derivatives of (iso) quinoline and quinazoline), the disclosures of which are hereby expressly incorporated by reference.

The use of these and similar ligands, native or synthetic, known or hereinafter discovered, is specifically within the scope of the present invention. Preferred ligands show high selectivity for the PTBR, relative to the benzodizepine receptors present in the brain (CBR) or GABA. In competitive binding experiments, the difference in binding affinity is preferably at least 10-fold, more preferably at least 100-fold, most preferably at least 1000-fold.

PTBR ligands include agonist and antagonist of PTBR. Representative PTBR agonists include benzodiazepines, e.g. Ro5-4864 and its derivatives, while representatives PTBR antagonists include isoquinoline carboxamides, e.g. PK 11195 and PK 14105 (a nitrophenyl derivative of PK 1195), and further derivatives.

B. Screening for new antagonists and agonists of PTBR a. Identifying New PTBR Ligands The first step in identifying new ligands of the PTBR (whether agonists or antagonists), is in vitro screening to identify compounds that selectively bind the peripheral-type receptor. Receptor-binding can be tested using peripheral-type and brain-derived receptors isolated from their respective native sources, or produced by recombinant DNA technology and/or chemical synthesis. The binding affinity of the candidate compounds can be tested by direct binding (see, e.g. Schoemaker et al., *J. Pharmacol. Exp. Ther.*, 285:61–69 [1983]) or by indirect, e.g. competitive, binding. In competitive binding experiments, the concentration of a compound necessary to displace 50% of another compound bound to the receptor ($IC_{50}$) is usually used as a measure of binding affinity. The other ligand can be any compound known to bind to PTBR with high affinity and selectivity, e.g. PK11195 or Ro5-4864.

In a specific embodiment, in order to identify novel ligands, DNA encoding the full length sequence of the human peripheral benzodiazepine receptor (GenBAnk M36035) is cloned into an expression vector containing a selectable marker. The vector is used to transfect recombinant host cells, for example mammalian cells, e.g., the human embryonic kidney cell line (HEK-293). Following several rounds of selection stable lines which express PTBRs are identified by Western blot using immunoreactivity toward an epitope tag that is genetically engineered into the PTBR gene. Membrane fractions are prepared from the stably expressing cell lines in bulk and stored frozen for HTP screening. Authentification of the PTBR containing membrane fractions is achieved by reproducing binding coefficients of known radiolabelled ligands (such as [3H] Ro5-4864). Screening for novel ligands is performed by virtue of their ability to compete effectively with [3H]Ro5-4864 in competitive binding assays. Binding coefficients can be determined by any known manner, e.g. by Scatchard analysis.

b. Distinguishing Between Ligands Acting as Agonists and Antagonists, Respectively The second step is distinguishing between PTBR agonists and antagonists. This can be done in in vitro or in vivo experiments, by monitoring the response of a cell following the binding of the ligand to the receptor. An agonist will produce a cellular response, which results in increased or new activity or in the inhibiting of an already occurring cellular activity. In contrast, an antagonist will have no effect on cellular response, rather will have the effect of preventing binding of agonists to the same receptor sites. It may be desirable to screen for antagonists in a fashion that the readout is functional to find molecules that activate the receptor without affecting the binding site(s) of the native ligand(s). Antagonists can be screened in a similar fashion.

For example, the following methods are suitable for identifying antagonists and agonists of the PTBR:

1. Inotropic response of isolated rat hearts.

Hearts are perfused using a Langendorff apparatus and contraction measured as the left ventricular pressure. A latex balloon filled with water is inserted into the left ventricle measuring the oscillations in the force of the heart beat. This is quantitated by attachment to a Gould Statham pressure transducer (P23ID) by continuous measurement. After equilibration, experiments commence by the administration of the test compound to the perfusate. I notropic response is expressed as a percentage change in contractile force, measured when either maximum increase or depression was observed, as compared to the force immediately before administration of test compound. Agonists to the PTBR will induce a positive inotropic response, while antagonists to the PTBR will induce a negative inotropic response.

2. Inotropic response of atrial muscle strips.

Muscle strips from the right auricle of human hearts (where available) are excised before patients are connected to a cardiopulmonary bypass. Strips are emersed in a tissue bath containing oxygenated Krebs-Heinseleit buffer and stimulated at 1.5 Hz via two platinum electrodes with rectangular wave pulses of 10 ms duration, 15 V above threshold. Contraction parameters are sampled every 5 minutes of stimulation for no longer than 90 minutes following tissue harvesting. Agonists of the PTBR will have a negative inotropic response, while antagonists of the PTBR will have a positive inotropic response.

3. A similar approach can be taken using atrial strips of guinea pig.

4. Using echocardiography it is possible to measure cardiac function in rats in vivo following administration of putative PTBR agonists and antagonists.

5. Monitoring vagal tone, as determined by quantification of the amplitude of respiratory sinus arrhythmia, can be used to identify PTBR agonists in a suitable animal model. In this instance one would expect a PTBR agonist to depress vagal tone.

6. Agonists and antagonists can also be identified in in vitro tissue culture screens for agonists and antagonists of PTBR Incubation of rat cardiomyocytes with PTBR agonists stimulates protein and ANP synthesis. Antagonists can be identified based on their ability to negate a known effect of an agonist.

C. Other PTBR Antagonists

The PTBR antagonists of the present invention are not limited to PTBR ligands. Other PTBR antagonists include (1) variants of a native PTBR that retain the ability to bind an endogenous PTBR ligand but are deficient in their ability to mediate a biological response, (2) soluble receptors, (3) antibodies specifically binding an endogenous PTBR ligand at or around its receptor binding site so that they block the binding of the ligand to its native receptor, and (4) selective inhibitors of the in vivo production of an endogenous PTBR ligand, such as transcriptional regulators of the expression of an endogenous PTBR ligand in vivo. Another preferred PTBR antagonist is a bioorganic molecule, usualy an orally active compound that is based on synthetic and/or molecular modeling studies, that is capable of preventing the interaction between a native PTBR receptor and its endogeneous ligand. Such PTBR antagonists can be identifying using the same type of assays as those discussed above.

D. Availability of PTBR Antagonists and Agonists

The PTBR antagonist and agonists of the present invention can be small molecules, e.g. organic compounds or peptides that can be synthesized by known techniques of chemical synthesis. Some PTBR antagonists or agonists will be polypeptides, e.g. native sequence PTBR ligands, or fragments, variants or derivatives thereof, and may be produced by recombinant DNA technology, chemical synthesis or a combination of these or similar techniques. Some PTBR agonist or antagonists are commercially available, e.g. from Hoffmann-La Roche AG (Nutley, N.J.), and Synthelabo, France.

The PTBR agonists and antagonists of the present invention may also be antibodies that specifically bind PTBR or (in the case of PTBR antagonists) an endogenous PTBR ligand. Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

According to one approach, monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. Preferred immortalized cell lines are those that fuse efficiently, support stable high level expression of antibody by the selected antibody-producing cells, and are sensitive to a medium such as HAT medium.

The culture medium in which the hybridoma cells are cultured can then be assayed for the presence of monoclonal antibodies directed against the particular PTBR or endogenous PTBR ligand used. Preferably, the binding specificity of monoclonal antibodies produced by the hybridoma cells is determined by immunoprecipitation or by an ill vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown ill vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, monoclonal antibodies may be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells discussed above serve as a preferred source of such DNA. Once isolated, the DNA may be placed into expression vectors, which are then transfected into host cells such as COS cells, Chinese hamster ovary (CHO) cells, or myeloma cells that do not otherwise produce immunoglobulin protein, to obtain the synthesis of monoclonal antibodies in the recombinant host cells.

The antibodies, including antibody fragments, such as Fv, Fab, Fab', F(ab')$_2$ or other antigen-binding subsequences of antibodies, may be humanized. Humanized antibodies contain minimal sequence derived from a non-human immunoglobulin. More specifically, in humanized antibodies residues from a complementary determining region (CDR) of a human immunoglobulin (the recipient) are replaced by residues from a CDR of a non-human species (donor antibody) such as mouse, rat or rabbit having the desired specificity, affinity and capacity. In some instances, Fv framework residues of the human immunoglobulin are also replaced by corresponding non-human residues. Humanized antibodies may additionally comprise residues that are found neither in the recipient antibody nor in the imported CDR or framework sequences [Jones et al., *Nature,* 321:522–525 (1986); Riechmann et al., *Nature,* 332:323–329 (1988)].

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature,* 321:522–525 (1986); Riechmann et al., *Nature,* 332:323–327 (1988); Verhoeyen et al., *Science,* 239:1534–1536 (1988)], by substituting rodent CDRs or CDR sequences for the corresponding sequences of a human antibody. In addition, human antibodies can be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

The antibodies may be bispecific, in which one specificity is for a PTBR, and the ther specificity for another protein, such as, a second, different PTBR, or a different epitope of the same PTBR or a PTBR ligand.

E. Compositions Comprising PTBR Ligands

The PTBR ligands (agonists or antagonists) can be administered to a patient at therapeutically effective doses to treat (including prevention) a specifically circulatory, e.g. cardiac disease, such as, cardiac hypertrophy. A therapeutically effective dose refers to that amount of the compound sufficient to result in desired treatment.

Toxicity and therapeutic efficacy of such compounds can be determined by standard pharmaceutical procedures in cell cultures or experimental animals, eg., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound, which achieves a half-maximal inhibition of symptoms) as determined in cell culture. Such information can be used to accurately determine useful doses in humans. Levels in plasma can be measured, for example, by high performance liquid chromatography. A typical daily dose for a PTBR agonist or antagonist of the present invention might range from about 1 $\mu$g/kg to about 100 mg/kg of patient body weight or more per day, depending on the factors mentioned above, preferably about 10 $\mu$g/kg/day to 10 mg/kg/day.

Pharmaceutical compositions for use in accordance with the present invention can be formulated in conventional manner using one or more physiologically acceptable carriers or excipients. Thus, the compounds and their physiologically acceptable salts and solvates can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate. talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional maimer.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethaane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

If an agonist or an antagonist is coadministered with another agonist or antagonist, or with another agent having similar biological activity, the different active ingredients may be formulated together in an appropriate carrier vehicle to form a pharmaceutical composition. The PTBR antagonists of the present invention may, for example, be combined or otherwise coadministered with other therapeutics used in the treatment of cardiac hypertrophy or associated cardiac conditions or symptoms, including ACE inhibitors, CT-1 inhibitors, hGHG, IGF-1, endothelin, leukocyte inhibitory factor (LIF), differentiation-inducing factor (DIF, D-factor), melanoma-derived LPL inhibitor (LMPLI), natriuretic peptides, e.g. brain natriuretic peptide (BNP) and atrial natriuretic peptide (ANP).

The following examples illustrate, but do not limit, the invention. All references cited throughout the specification, including the examples, are hereby expressly incorporated by reference.

EXAMPLE 1

Differential Expression of PTBR is Various Models of Cardiac Disease

1. In Vivo Model of Cardiac Hypertrophy

Rats with left ventricular hypertrophy (LVH) were produced essentially as described in Schunkert et al., 1990, supra. Left ventricular hypertrophy (LVH) was induced by pressure overload as a result of constriction of the ascending aorta. A stainless steel clip of 0.6-mm internal diameter was placed on the aorta of anesthetized weanling rats. Control animals underwent thoracotomy as a sham operation. Animals recovered from surgery and appeared healthy until 20 weeks when a few animals were in demise likely due to heart failure, which typically occurs at this point (Schunkert et al., 1990, supra). The animals were sacrificed and hearts examined 10 weeks and 20 weeks post-operation. Hypertrophy was evident at both time points as determined by changes in left ventricle weight and thickness (Table 1), similar to the findings of others. Aortic banded rats and sham operated control animals were sacrificed and measured for heart weight, left ventricle (LV) weight, left ventricle thickness, and LV weight/body weight. There were 6 animals per group. Data are expressed as average with standard deviation in parentheses.

TABLE 1

|  | Heart weight Grams (stdev) | LV weight Grams (stdev) | LV thickness Mm (stdev) | LV wt/body wt Mg/g (stdev) |
|---|---|---|---|---|
| 10 Week |  |  |  |  |
| Sham (n = 6) | 1.000 (0.112) | 0.654 (0.052) | ND | 1.675 (0.125) |
| Banded (n = 6) | 1.205 (0.074) | 0.909 (0.052) | ND | 2.269 (0.104) |
| P value | 0.004 | 0.00001 |  | 0.000004 |
| 20 Week |  |  |  |  |
| Sham (n = 6) | 1.053 (0.074) | 0.734 (0.049) | 1.700 (0.089) | 1.610 (0.073) |
| Banded (n – 6) | 1.273 (0.293) | 0.931 (0.260) | 2.067 (0.258) | 1.962 (0.344) |
| P value | 0.1 | 0.1 | 0.008 | 0.03 |

LVH rats were examined for expression of ANP mRNA which, according to published data (Schunkert et al., 1995, supra), should increase in the diseased animals. mRNA was extracted from the left ventricle of each animal and analyzed by Northern blot (FIG. 1). ANP transcripts were significantly elevated (5~fold) at 10 weeks and 20 weeks relative to normal. The levels of mRNA were examined for BNP (FIG. 1), cardiac (α-actin (not shown) and β-myosin heavy chain (not shown) by Northern blot and, as expected, these were also elevated in the diseased animals. Blots were probed for cyclophilin transcripts to attest to equal loading of mRNA. This molecular and physical data confirm that the banded rats were pressure overloaded and responded with cardiac hypertrophy. Poly A+mRNA was prepared from each of the animals, as described herein, for assessment of differentially expressed genes in the disease state, using microarray analysis in a preferred embodiment. A summary of the findings of the microarray analysis is provided in FIG. 4, and described in detail below.

2. In Vivo Model of Viral Myocarditis

In another representative example, an in vivo model of cardiac disease, specifically, viral myocarditis, was used within the context of the present invention. CVB3 infection in mice results in myocardial disease progression, which was used as a model for examination of the pathogenesis of virus-induced human myocarditis. The virus is directly injurious to myocardial cells early following infection during the preinflammatory period as determined by light and electron microscopic cytological assessment (Arola et al., *J. Med. Virol.* 47:251–259 (1995); Chow et al., *Lab. Invest.* 64:55– 64 (1991); McManus et al., *Clin. Immunol. Immunopathol.* 68:159–169 (1993); Melnick et al., *J. Expert. Med.* 93:247–266 (1951)). Beginning by day two post-infection cytopathic lesions are evident in ventricular myocytes, characterized by cell vacuolar changes, contraction bands and coagulation necrosis (McManus et al., supra). By day 5 post-infection this myocardial injury becomes obscured by inflammatory infiltrates, cellular calcification, and tissue edema.

A/J (H-2$^a$) mice (Jackson Laboratories, Bar Harbor, Maine) were 4 weeks of age when received at St. Paul's Hospital Animal Care Facility, University of British Columbia. Mice were acclimatised for one week in a St. Paul's Hospital Animal Care Facility level 2 biohazard containment room prior to the onset of the experiment. Any mice that died naturally during the course of the disease were not included in groups of mice to be used for RNA extraction. Mice were euthanized by $CO_2$ narcosis.

Myocarditic CVB3 was kindly provided by Dr. Charles J. Gauntt (University of Texas, San Antonio, Tex.) and was stored at –80° C. Virtis was propagated in HeLa cells (American Type Tissue Culture Collection, Rockville, Md.) and is routinely titred before the onset of all experiments using the plaque assay method, with modifications as previously described (Anderson et al., *J. Virol.* 70:4632–4645 (1996)).

Adolescent A/J mice were infected with $1 \times 10^5$ pfu of myocarditic CVB3 or PBS sham and euthanized on days 3, 9, and 30 post-infection. Ten to fifteen mice per group (CVB3 infected or sham injected) per time-point (days 3, 9, and 30) were euthanized and heart muscle was removed. Following a wash in sterile phosphate buffered saline, a small portion of the apex of the heart was removed and fixed in 4% paraformaldehyde. The remainder of the heart was flash frozen in liquid nitrogen and stored at –80° C. for future RNA isolation.

Sections from the heart were fixed in fresh DPBS-buffered 4% paraformaldehyde overnight at 4° C. Fixed tissue was dehydrated in graded alcohols, cleared in xylene, embedded in paraffin, and sectioned for hematoxylin and eosin, and Masson's trichrome stains. Serial sections were also prepared for in situ hybridization and nick-end labelling stained. The extent and severity of virus-induced injury (including coagulation necrosis, contraction band necrosis, and cytopathic effects), inflammation, and tissue fibrosis and calcification was evaluated and scored as previously described (Chow et al., supra).

In situ hybridization for CVB3 viral RNA localization was carried out as previously described (Anderson et al., Supra; Hohenadl et al., Mol. Cell. Probes 5:11–20 (1991)). Briefly, tissue sections were incubated overnight in hybridization mixture containing digoxigenin-labelled, CVB3 strand-specific riboprobes. Post-hybridization washing was followed by blocking with 2% normal lamb serum. A sheep anti-digoxigenin polyclonal antibody conjugated to alkaline phosphatase (Boehringer Mannheim PQ, Laval, Canada) was developed in Sigma-Fast nitroblue tetrazolium-BCIP [5-bromo-4-chloro-3-indolylphosphate tuluidinium] (Sigma Chemical Co.). The slides were counterstained in fresh carmalum and examined for reaction product by light microscopy. Poly A+mRNA was prepared from each of the animals, as described herein, for assessment of differentially expressed genes in the disease states, using microarray analysis in a preferred embodiment. A summary of the findings of the microarray analysis is provided in FIG. 4, and described in detail below.

3. In Vivo Model of Myocardial Infarction a. Left Ventricle Myocardial Infarction In yet another representative example, an in vivo model of cardiac disease, specifically, left ventricle myocardial infarction, was used within the context of the present invention. The rat myocardial infarct (MI) model used is described by Pfeffer et al., Circ. Res. 57:84–95 (1985).

Male Sprague-Dawley rats at age 7–10 weeks were anesthetized with ketamine (80 mg/kg. IP) and xylazine (10 mg/kg. IP). The thorax and abdomen was shaved, after which the areas were scrubbed with providone-iodine and 70% isopropyl alcohol a minimum of three times, beginning at the incision line and continuing in a circular motion proceeding toward the periphery. The rats were intubated and placed on a respirator with room air at a rate of 55 breaths/min. A left thoracotomy was performed between the fourth and fifth ribs, after which the heart was exteriorized and the left anterior descending coronary artery (LAD) ligated with silk suture. The same surgical procedure was employed for sham-operated rats, however, the suture was passed through the left ventricular wall and the LAD was not occluded.

Following the surgical procedure, negative pressure in the thoracic was quickly reestablished and the wound closed with a purse-string suture using 3-0 non-absorbable suture material. Butorphanoll (0.1 mg/kg. SQ) was provided post surgery as a prophylactic analgesic. The rats were extubated when they recovered their gag reflex and allowed recovering in a warming chamber.

Seventy-five percent of the rats had large infarcts on their left ventricle free walls and perioperative mortality rate is about 50%, which is comparable to the published data. The heart weight as a percentage of body weight 3–4 weeks post-infarction is increased (see table).

TABLE 2

| Group | No. of Rats | Heart Weight (mg) | Body Weight (g) | HW/BW (mg/g) |
|---|---|---|---|---|
| Sham | 4 | 121.38 +/− 0.09 | 419.23 +/− 62.77 | 2.92 +/− 0.23 |
| Large MI Infarction | 5 | 141.83 +/− 0.74 | 414.06 +/− 49.94 | 3.54 +/− 0.40 |

Tissue was collected 2 week, 4 week, 8 week, 12 week and 16 week post-surgery. Blood was collected the day before surgery and the day before sacrifice for measurement of plasma ANP level. On the day of necropsy, each heart was divided transversely into two halves so that the infarcted area is bisected. One half of the heart was used for histological evaluation, and the other for mRNA microarray analysis. Poly A+mRNA was prepared from each of the animals, as described herein, for assessment of differentially expressed genes in the disease state, using microarray analysis in a preferred embodiment. A summary of the findings of the microarray analysis is provided in FIG. 4, and described in detail below.

b. Septum Myocardial Infarction

In another representative example, septum tissue was obtained from diseased rat hearts obtained through the left ventricle rat MI model of Pfeffer et al., as described above. Poly A+mRNA was prepared from each of these septums, as described herein, for assessment of differentially expressed genes in the disease state, using microarray analysis in a preferred embodiment. A summary of the findings of the microarray analysis is provided in FIG. 4, and described in detail below.

4. Preparation of Normalized cDNA Libraries for Microarray Analysis

To capture as many different genes as possible without the necessity to include all such genes, clones may be randomly picked from a cDNA library, resulting in redundant selection of genes expressed at high and moderate abundance. It is estimated that 50% of all transcripts in a cell derive from ~400 genes (Bishop et al., Nature 250(463):199–204 (1974)). Thus, random picking of 20,000 cDNA clones would represent roughly half that number of different genes, and rare transcripts may be underrepresented.

However, a greater number of different clones can be randomly chosen for microarray analysis if cDNA libraries produced from the models of the present invention are first normalized. Methods have been developed to construct libraries that bring the frequency of all clones to near equivalence (Soares et al., Proc. Natl. Acad. Sci. USA 91(20):9228–32 (1994); Bonaldo et al., Genome Res. 6(9):791–806 (1996)), thus minimizing redundant picking of prevalent clones. In addition, selecting clones from a normalized library also increases the likelihood of choosing clones of rare transcripts.

Following the method of (Bonaldo et al., supra), a normalized version of a cDNA library was generated from normal tissue, cells or blood (e.g., the left ventricle of normal rat). In a particular embodiment, poly A+RNA was purified from the tissue samples provided by the in vivo disease models described above. A directionally cloned cDNA library was first generated by conventional methods. Briefly, double stranded cDNA was generated by priming first strand synthesis for reverse transcription using oligo dT primers which contain a Not I restriction site. After second strand synthesis, Xba I adapters are added to the 5' end of the cDNA, and the cDNA size was selected for >500 bp and ligated into the corresponding restriction sites of phagemid vector pCR2.1 (Invitrogen, San Diego Calif.).

From the total cDNA library, a normalized library was generated as detailed elsewhere (Bonaldo et al., supra) and described here briefly. Phagemid vector pCR2.1 contains an F1 origin of replication. Thus, the cDNA library can be propagated as single stranded phage with appropriate helper virus. Single stranded, circular DNA was extracted from the phage library and serves as "tester" DNA in the hybridization step of normalization. The other component of the hybridization, "driver" DNA, was generated from the library by PCR amplification using a set of primers specific for the region of the vector, which flanks the cloned inserts. Purified tester DNA (50 ng) and driver DNA (0.5 $\mu$g) was combined in 120 mM NaCl, 50% formamide, 10 mM Tris (pH 8.0), 5 mM EDTA, and 1% SDS. A pair of oligonucleotides (10 $\mu$g each), corresponding to polylinker sequence (same strand as tester DNA) which is present in the PCR product, was included in the hybridization reaction to block annealing of vector-specific sequences which are in common between tester and driver DNA.

The reaction mixture, under oil, was heated 3 min. at 80° C., and hybridization performed at 30° C. for 24 hr (calculated $C_0t$~5). Single stranded circles were purified from the reaction mixture by hydroxylapatite (HAP) chromatography, converted to double strand DNA, and electroporated into bacteria to yield a normalized cDNA library representative of genes expressed in the left ventricle of rat. To evaluate the effectiveness of the normalization protocol, the frequency of a few clones (ANP, BNP, actin, and myosin) was assessed in both in the starting library and the normalized library. The frequency of abundant cDNAs (actin and myosin) was reduced and roughly equivalent to rarer cDNA clones (ANP and BNP). Clone frequency in the two libraries was determined with standard screening techniques by immobilizing colonies onto nylon membranes and hybridizing with radiolabeled DNA probes.

Certain genes, unexpressed in a normal tissue and turned on in diseased tissue, may be absent from the normalized cDNA library generated from normal tissue. To obtain disease-specific clones to include on the microarray, one can repeat the normalization strategy outlined above using diseased tissue obtained from the appropriate disease model. However, since most genes are expressed commonly between normal and diseased tissue, microarraying normalized libraries from diseased and normal tissue may introduce significant redundancy. In a preferred embodiment, clone redundancy is reduced, yet cDNAs are obtained which are expressed specifically, as well as substantially elevated, in diseased tissue. To obtain disease-specific cDNAs, a subtracted library can be made using protocols similar to those used to generate normalized libraries. Again, the method of Bonaldo et al., supra, described here briefly is used.

To make a subtracted library, a total cDNA library is generated from the tissue obtained from the disease model (e.g., left ventricle taken from a hypertrophic rat (10 week aortic banded)). The cDNA library is directionally cloned in pCR2.1 vector and single stranded tester DNA derived as described above for library normalization. The driver DNA is generated by PCR amplification of cloned inserts from the total cDNA library prepared from the left ventricle of normal rat. Hybridization occurs between sequences, which are in common to normal and diseased hearts. For this subtracted library, the reaction is driven more thoroughly (calculated $C_{ot}$~27) than normalization by using more driver (1.5 µg vs. 0.5 µg) and longer hybridization time (48 hr vs. 24 hr). Purification of nonhybridized, single stranded circles by HAP chromatography, conversion to double strand DNA, and electroporation into bacteria yields a subtracted cDNA library enriched for genes which are expressed in diseased rat hearts. To test that the library is truly subtracted, colony hybridization is performed with probes for ANP, BNP, actin, and myosin. The subtracted library has a high frequency of ANP and BNP clones since they are elevated significantly in the hypertrophic rat heart. Actin and myosin clones are absent since they are expressed equally in normal and diseased left ventricle.

In use of an exemplary normalized library within the context of the present invention, from two rat left ventricle cDNA libraries, 30,000 clones are picked for microarraying. 25,000 clones are taken from the normalized library generated from normal rats, and 5,000 from the subtracted library made from hypertrophic rats. The subtracted library should be less complex (i.e., fewer unique clones) than the normalized library, therefore, fewer clones need be picked. If, as estimated, only about 1% of all 20,000 genes are unique to the disease state, then the complexity would be only about 200, thus picking 5000 would likely yield a representative of each.

Preferably included on the microarray with the 30,000 unidentified genes are a set of known clones. Rat clones for the list of genes were isolated by PCR amplification from cDNA libraries using specific primer pairs. These known clones were included because they represent genes of particular interest and help evaluate the sensitivity of the microarray methodology. Indeed, any genes of particular interest may be included on such microarrays. By way of example, ANP, BNP, endothelin, β-myosin heavy chain, and α-actin are genes that change expression levels in the LVH model, and thus they serve as useful positive controls in the in vivo model exemplified herein.

5. Microarray Production From Model DNA

High quality DNA is important for the microarray printing process. DNA was generated by PCR amplification of the cDNA insert from clones. 10,000 clones per array were generally used. Indeed, it is preferable to use a robust method of template preparation, preferably accomplished in 96-well plates.

Figure 2:
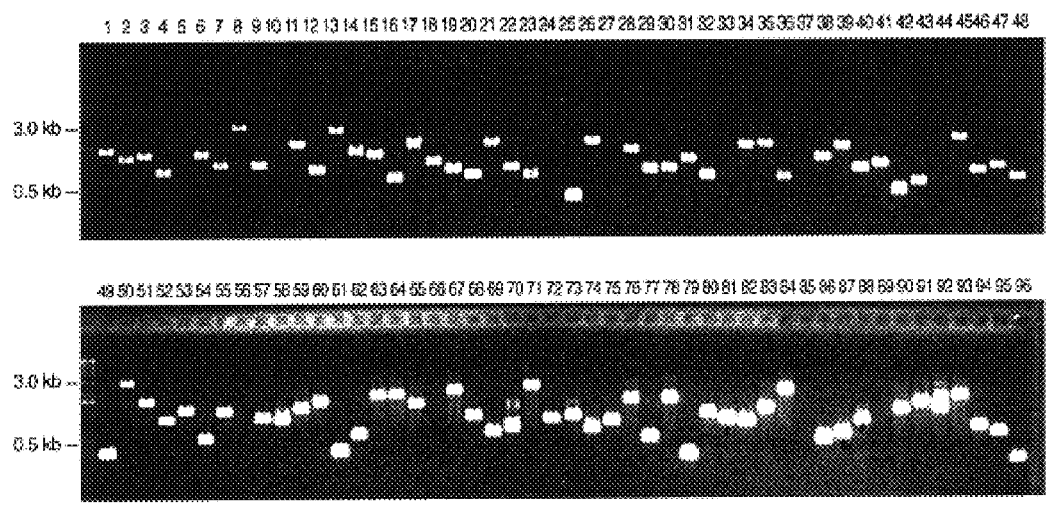
FIG. 2 shows PCR amplified DNA from 96 random clones of rat left ventricle. PCR product (10% of total) from 96 clones was loaded onto a 1.0% agarose gel and visualized by ethidium bromide staining.

A microtiter plate protocol for PCR amplification of DNA and its subsequent purification was established that provides acceptable quality and quantity of DNA for printing on microarrays for use in a preferred embodiment of the present invention. Specifically, PCR primers were synthesized that amplify insert DNA from the vector pCR2.1, which was used for library construction. After 30 cycles of amplification each PCR product was passed over a gel filtration column to remove unincorporated primers and salts. To maintain robustness, the columns were packed in 96-well filter plates and liquid handling was performed robotically. The yield, per PCR reaction, is generally 2–5 µg, enough DNA for printing several hundred chips. FIG. 2 shows a gel containing purified PCR products from a single plate of 96 rat cDNA clones. In some samples no amplified DNA was produced (e.g., #37 and #44) and, in some cases, the size of the product indicated that the plasmid lacked an insert (e.g., #49 and #61).

To test the quality of DNA that was prepared by this PCR method, 96 purified samples from a single microtiter plate were produced as a microarray. Using a robotic liquid handler (Biomek 2000, Beckman), 85 µl of PCR reaction mixture was aliquoted into each well of a thin walled, 0.2 ml 96-well plate. The reaction mixture contained 0.2 mM each dNTP, 1.25 units of Taq polymerase, and 1X Taq buffer (Boehringer Mannheim). Primers, 1 µm each, are from vector regions, which flank the cloning site of pCR2.1 and include a 5' primary amine with a 6 carbon linker to facilitate attachment of DNA product to the glass surface of the microarray chip. 1.0 µl of bacterial culture of individual cDNA clones was added to each well. PCR conditions are: 2 min., 95° C. to denature, then 30 cycles of 950, 30 sec. / 65° C., 40 sec. / 72° C., 1 min. 30 sec., and a final extension of 72° C., 5 min. using a MJResearch PTC 100 thermocycler.

PCR products were purified by gel filtration over Sephacryl 400 (Sigma). Briefly, 400 µl of pre-swollen Sephacryl 400 was loaded into each well of a 96-well filter plate (PallBiosupport) and spun into a collection plate at 800 g for 1 min. Wells were washed 5 times with 0.2×SSC. PCR reaction mixtures were loaded onto the column and purified DNA (flow-thru) was collected at 800 g for 1 min. Samples are dried down at 50° C. overnight and arrayed.

Fluorescent probe pairs were synthesized by reverse transcription of poly A+RNA using, separately, Cy3 dCTP and Cy5 dCTP (Amersham). In 16.5 µl, 1 µg poly A+RNA and 2 µg of oligo dT 21 mer, were denatured at 65° C., 5 min. and annealed at 25° C., 10 min. Reverse transcription was performed for 2 hours at 37° C. with Superscript RT (Life Technologies, Gaithersburg, Md.) in 1× buffer, 10 units RNase block, 500 µM each dATP/dGTP/dTTP, 280 µM dCTP, 40 µM Cy5 or Cy3 dCTP, and 200 units RT. RNA is degraded in 0.1 M NaOH, 65° C. for 10 min. Labeled cDNA was purified by successive filtration with Chroma Spin 30 spin columns (Clontech) following manufacturer's instructions. Samples were dried at room temperature in the dark using a covered Speed-Vac. Probes were applied to the test chip for hybridization and the data collected essentially as described in Schena et al., supra. The intensity of hybridization signal at each element reflected the level of expression of the mRNA for each gene in the rat ventricle. Digitized signal data was stored and prepared for analysis. The data from this experiment is presented in FIG. 3.

Figure 3:
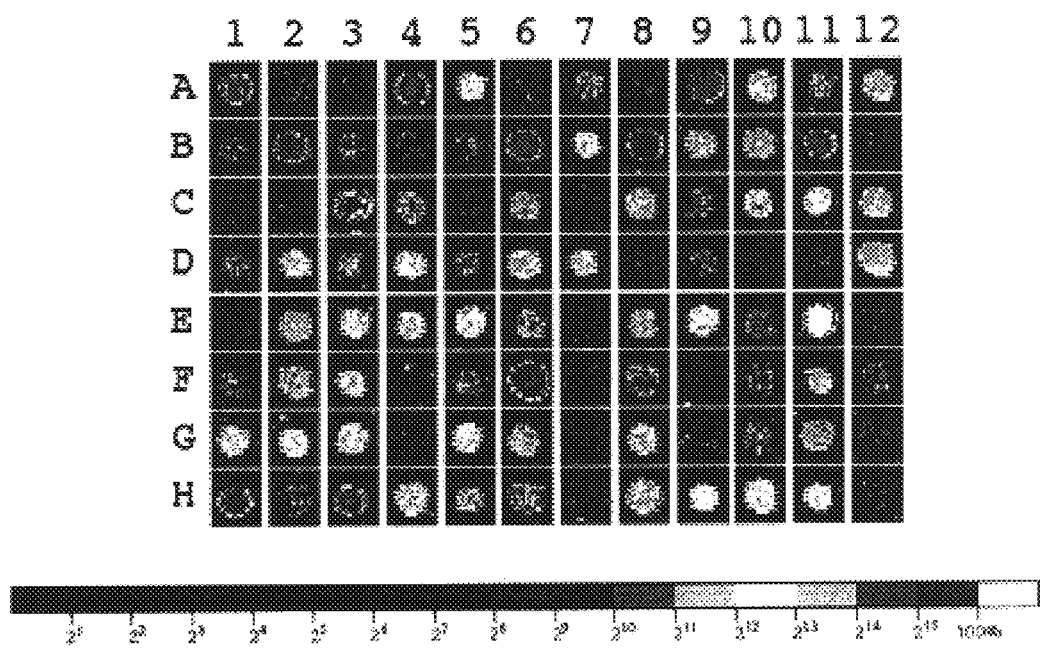
FIG. 3 shows a microarray analysis of 96 clones expressed in rat heart. Randomly chosen clones from a rat left ventricle cDNA library were printed onto a microarray and hybridized with Cy5-labeled rat left ventricle cDNA. The intensity of each probe is expressed in pseudo-color according to the scale shown. Blank spots resulted from lack of PCR amplifiable insert DNA from the corresponding clone.

Referring to FIG. 3, positive signals were detected from most of the elements that contained DNA. A series of control DNA elements were included on each chip to ensure consistency in labeling and hybridization between experiments and to aid in balancing the signal when two fluorescence channels are used. For each element hybridized with dual labeled probes, absolute and relative intensity of signal was determined. The results from these and other experiments indicate that these methods for production of template DNA and labeled cDNA probes are suitable for generating high quality microarrays within a preferred embodiment of the methods of the present invention. The evaluation of tens of thousands of genes for expression generates a large amount of data that can be manipulated by commercially available software packages that facilitate handling this type and quantity of data. The expression data can be stored, analyzed, and sorted from each experiment using this software. In addition, expression of each clone can be tracked from experiment to experiment using known methodologies.

6. Detection of Differentially Expressed Genies Using Microarray Analysis

Using cDNA obtained from the representative in vivo cardiac hypertrophy model, the in vivo viral myocarditis model, the in vivo left ventricle myocardial infarction model, and the in vivo septum myocardial infarction model, microarrays were constructed and probed as described above.

FIG. 4 provides a detailed summary of the characteristics of twelve differentially expressed disease genes. The expression data provided relates to the counterpart gene expressed in the in vivo models described supra, and shows the differential expression data of representative genes obtained through the disease models of the present invention and determined via microarray analysis.

Specifically, FIG. 4 provides the clone identification number for the differentially expressed model gene. As discussed in detail below, and as shown in FIG. 4, those representative disease model differentially expressed genes were found to correspond to human genes encoding 1–8U, prostacyclin-stimulating factor, osf-2, tissue specific mRNA, insulin-like growth factor binding protein 6, OSF-1, gas-1, YMP, BTG2, pre-B cell stimulating factor homolog (SDF1a), peripheral-type benzodiazepine receptor (PTBR), and cellular ligand of annexin II (p11). As disclosed in detail above, probes were applied to the microarrays for hybridization and the data collected essentially as described in Schena et al., supra. The intensity of hybridization signal at each element reflected the level of expression of the mRNA for each gene. For each element hybridized with dual labeled probes, absolute and relative intensity of signal is determined, which translates into the relative expression levels of the subject genes. The numeric data provided in FIG. 4 reflects the relative expression level of the gene in the disease state as compared to the expression level of the gene in the normal, or non-disease state, in the five representative disease state models delineated above and as determined by microarray analysis. Specifically, the data shown in FIG. 4 provides a positive or negative multiple of the expression level of the gene in the disease state, as compared to the normal state in the representative models.

Data are reported as differential expression values with positive numbers indicative of genes expressed at higher levels in the diseased tissue relative to normal tissue, and negative values indicative of lower expression in disease. Data are the average values from multiple experiments performed with separate DNA arrays (n=4 for MI left ventricle and septum, n=2 for viral myocarditis, and n=2 a for LVH). Array probes were generated from RNA pooled from multiple animals (n=4 for MI, n=10–15 for myocarditis, and n=3 for LVH).

The data also reflects expression levels of genes in certain disease models over various time points. For example, gene expression in the myocardial infarction model was compared at 2, 4, 8, 12, and 16 weeks for the representative genes in the disease state versus the normal state. Indeed, such experimentation provides valuable data regarding the temporal relationship of gene expression levels in disease states and provides important insights regarding the treatment, diagnosis, and modulation of differentially expressed disease state genes, as discussed in detail infra.

One to two percent of the clones assayed on microarrays were found to be differentially expressed. Secondary chips may be used for more extensive hybridizations, including examination of individual animals, and more thorough evaluation of time points. In a preferred embodiment, clones that reproducibly scored in microarray analysis to be at least about two-fold elevated or decreased were microarrayed on separate secondary chips and their expression levels determined. It is understood, however, that differentially expressed genes exhibiting less than about a two-fold change in expression, e.g., less than one, one-half, or one-quarter, or greater than about a two-fold change in expression, e.g., greater than three, five, ten, twenty, one hundred-fold, or one thousand-fold, are within the scope of the present invention.

7. Identification of Differentially Expressed Human Genes

Differentially expressed clones obtained from the microarray analysis of DNA obtained from the disease models described above were sequenced and compared to known human gene sequence databases for matches to known human genes. FIG. 5 shows alignment data comparing the cDNA encoding the differentially expressed rat P0268 gene with human cDNA corresponding to PTBR (SEQ ID NOs: 1 and 2). FIG. 6 shows the amino acid sequence of human PTBR.

EXAMPLE 2

Effect of a PTBR Agonist and Antagonist on Cardiac Hypertrophy in a Model of Neonatal Rat Cardiomyocytes 1. Isolation of Neonatal Rat Ventricular Cardiomyocytes Neonatal rat ventricular cardiomyocytes were isolated from one or two days old rat pups using the following reagents and isolation procedure:

Reagents

Dissociation buffer: CBFHH (Calcium- and Bicarbonate-Free Hanks with Hepes(, pH 7.5

NaCl 137 mM; KCl 5.36 mM; $MgSO_4 \times 7H_2O$ 0.81 mM; Dextrose 5.55 mM; $KH_2PO_4 \times 7H_2O$ 0.34 mM; Hepese 20 mM;

Penicillin 50U/ml and Streptomycin 50 $\mu$/ml 0.1% trypsin/0.001% DNaseII or I in dissociation buffer.

DNaseII-Sigma (V, EC3.1, 1,22.1, bovine spleen, filter (0.2 $\mu$m).

trypsin-1:250 from Difco Lab, Cat#0152-13-1, Lot:89568JK Serum-free medium: DMEM21/COON'S F12+1 mg/ml DBA+1XP/S Culture medium: DMEM21/COON'S F12+10% FBS+1X P/S Isolation Roll pups in a small amount of 75% ethanol, decapitate and cut the hoax open,isolate the heart and cut the ventricle out at AV groove and quickly remove to a 50 ml tube containing 30 ml CBFHH+0.3 ml heparin (1000 U/ml).

Transfer hearts to a 100-mm Petri dish, wash with CBFHH twice, trim ventricle and cut ventricle into 6–8 pieces.

Transfer heart tissues with wide tip 10 ml pipet to 50 ml tube. Add 10 ml CBFHH with 0.1% trypsin+0.001% DNaseII.

Rock for 10 minutes (do not over digest the cells).

Gently pipette the tissue 10X.

Let the tissue settle down, then discard the supernatant (mainly cell debris).

Repeat the dissociating procedure and collect the supernatant in a 50 ml tube containing 7 ml of FBS at room temperature (supernatant contains isolated cells). The whole dissociation requires 12–16X.

Collect all supernatant and spin down the pellet at 1000 rpm for 5–6 minutes at room temperature.

Wash the pellet once with DMEM21/COON'S F12+10% FBS+0.001% DNase, make sure than the pellet is well suspended.

Strain cells with a cell strainer (70 $\mu$M), pellet cells again.

Add 40 ml culture medium to the pellet (isolated from about 20 ventricles).

Preplate cells in 100-mm dish—10 ml/dish, for 30–45 minutes at 37° C.

Collect supernatant from the preplated plate (non-myocytes have already attached to the plate but myocytes still in suspension).

Wash the plated with 10 ml culture medium. Bang the empty plate 10 times to detach myocyte that may stick to the plate. Repeat this procedure 4x.

Count cells and determine viability.

Seed cells into fibronectin coated plates at a density of 0.1 million cells/cm$^2$ in culture medium and return to the incubator overnight.

The next day, change to serum-free medium for 24 hours.

Perform experimental incubations.

2. Monitoring Hypertrophy

When cardiomyocytes undergo hypertrophy several biochemical parameters can be monitored.

There is an increase in protein synthesis and atrial natriuretic peptide (ANP) synthesis and an upregulation of the $\beta$-myosin heavy chain gene. These three parameters were used to assess the effects of ligands of the peripheral-type benzodiazepine receptor (PTBR) upon neonatal rat cardiomyocytes.

Protein synthesis is assessed by including radiolabelled amino acids in the experimental incubation medias (i.e., [$^3$H]phenylalanine) at the end of the incubation the cell monolayer is washed with phosphate bufered saline, fized with 10% TCA and lysed with 0.25N NaOH. The total cell lysate is then assessed for tritium contant by scintillation spectrometry.

ANP content of cell culture supernatants is assessed by a competition ELISA assay that relies on the ability of ANP in the sample to compete effectively with a standard amount of [$^{125}$I]ANP for receptor binding.

To monitor the expression of $\beta$-MHC, a $\beta$-MHC promoter-luciferase reporter plasmid was constructed. This plasmid is inserted into the cardiomyocyte cultures by liposome mediated transfection and luciferase activity in cell lysates determined following incubation. The amount of luciferase actvity is directly proportional to the level of transcription of the $\beta$-MHC gene.

When cardiomyocytes undergo hypertrophy, their morphology changes quite drastically. The cells become larger and more spread out so another technique employed to monitor hypertrophic effects on cardiomyocytes is to assess their morphology and document that by photography.

Figure 8:
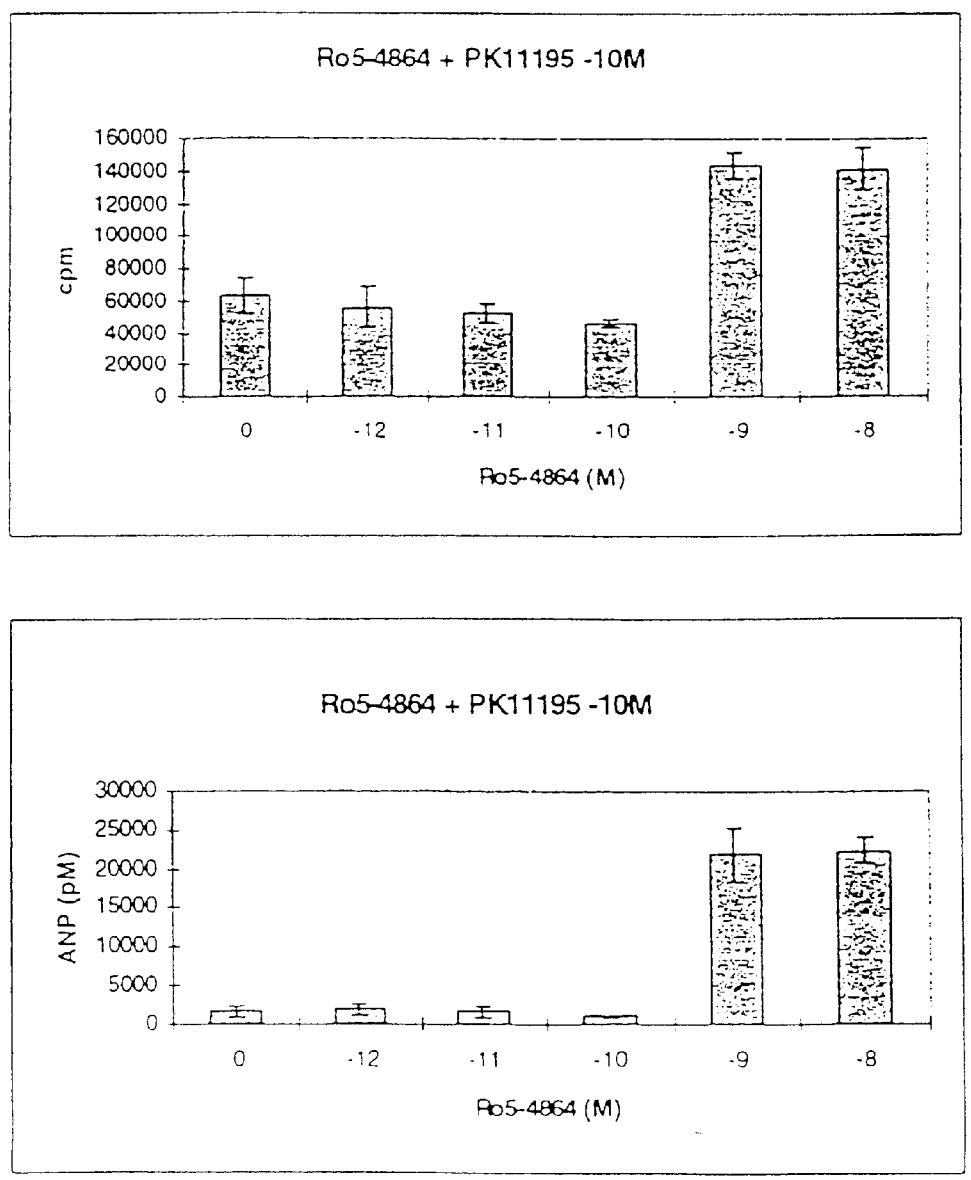
FIG. 8 shows the effect of PK11195 on the Ro5-4864 induced increase in protein an ANP synthesis in neonatal rat cardiomyocytes.

3. Results a. Neonatal rat cardiomyocytes were cultured in 24-well plates for 24 hours in serum-free medium. Medium was then removed and replaced with experimental culture medium containing [$^3$H]phenylalanine (10 $\mu$Ci/ml) and either the PTBR agonist Ro5-4864 (RBI, MA, USA) in a concentration range of $10^{-12}$–$10^{-8}$ M, or the PTBR antagonist PK11195 (RBI, MA, US) in a concentration range of $10^{-12}$–$10^{-8}$ M. Control incubations received [$^3$H] phenylalanine (10$\mu$Ci/ml) containing medium alone. Cell cultures were returned to the incubator for a further 48 hour incubation after which time the cell culture supernatants were harvested for ANP analysis and the cell monolayers were prepared for assessment of tritium incorporation. FIG. 7 shows that the PTBR antagonist PK11195 had no effects upon either protein synthesis (as assessed by incorporation of radiolabelled phenylalanine) or ANP synthesis (as assessed by a competition binding ELISA). However, at concentrations greater than or equal to $10^{-11}$ M, the PTBR agonist Ro5-4864 caused a three-fold increase in protein synthesis and a five-fold increase in ANP synthesis. Data are expressed as the mean +/– standard deviations of quadruplet samples.

b. Neonatal rat cardiomyocytes were cultured in 24-well plates for 24 hours in serum-free medium. Medium was then removed and replaced with experimental culture medium containing [$^3$H]phenylalanine (10 $\mu$Ci/ml) and either the PTBR agonist Ro5-4864 (RBI, MA, USA) in a concentration range of $10^{-12}$–$10^{-8}$ M, or the PTBR antagonist PK11195 (RBI, MA, US) at a concentration of $10^{-10}$ M. Control incubations received [$^3$H]phenylalanine (10 $\mu$Ci/ml) containing medium alone. Cell cultures were returned to the incubator for a further 48 hour incubation after which time the cell culture supernatants were harvested for ANP analysis and the cell monolayers were prepared for assessment of tritium incorporation. FIG. 8 shows that $10^{-10}$ M PK11195 prevented the Ro5-4864 induced increase in protein and ANP synthesis at concentrations of Ro5-4864 of $10^{-12}$–$10^{-10}$ M. However, at higher concentrations ($10^{-10}$–$10^8$ M) Ro5-4864 was able to overcome the inhibitory effect of PK11195 and caused the agonist induced increase in protein and ANP synthesis to return even in the presence of $10^{-10}$ M PK11195. Data are expressed as the mean +/– standard deviations of quadruplet samples.

c. Neonatal cardiomyocytes were cultures in 6-well plates overnight following isolation.

Figure 9:
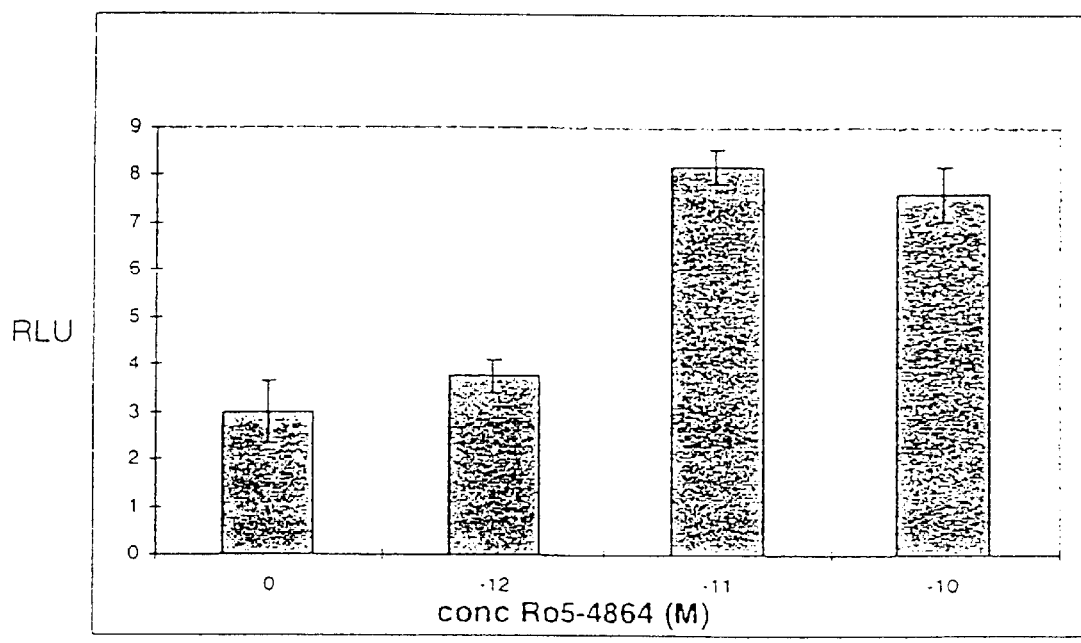
FIG. 9 shows the effect of Ro5-4864 on luciferase activity in neonatal rat cardiomyocytes.

The cell monolayers were then transfected with a $\mu$-MHC promoter-luciferase reported plasmid and a control plasmid to aid data normalization (pSEAP2 Clontech Corp) using lipofectamine liposome mediated plasmid delivery. Following recovery from the transfection, the cell cultures were treated for 24 hours in the presence and absence of the PTBR agonist Ro5-4864 at $10^{-12}$ M, $10^{-11}$ M and $10^{-10}$ M. The culture supernatants were then harvested for SEAP activity and cell lysates prepared for luciferase assay. Following normalization of the data to correct for transfection efficiency between cultures, FIG. 9 shows that at greater than or equal to $10^{-11}$ M concentration Ro-5-4864 caused a three-fold increase in luciferase activity that reflects a three-fold increase in transcriptional activity from the $\beta$-MHC promoter. Data are expressed as the mean standard derivations of triplicate samples.

d. Neonatal rat cardiomyocytes were cultures in 6-well plates overnight following isolation.

Cultures were then maintained in serum-free medium in the presence and absence of Ro5-4864 at $10^{-10}$ M. FIG. 10A shows a representative photograph of the control and treated cultures following 24 hours of culture and clearly shows the larger cell size of the cardiomyocytes that received Ro5-4864. FIGS. 10B and 10C show the same cultures following 96 hours of culture and the differenes between control and treated are quite striking. The treated cultures are much larger and adherent to the extracellular matrix while the control cultures at the same time point are small and rounded and beginning to disintegrate.

4. Conclusions

The PTBR agonist Ro5-4864 induces a strong hypertrophic response as assessed by a three- to five-fold increase in protein synthesis, ANP synthesis, transcription of the β-MHC gene reporter and by morphological assessment. This hypertrophic effect can be reversed by coincubation of Ro5-4864 with the PTBR antagonist PK11195.

What is claimed is:

1. A method for inducing a hypertrophic response in cardiac myocytes which comprises contacting said myocytes with an effective amount of an agonist of a peripheral-type benzodiazepine receptor (PTBR).

2. The method of claim 1 wherein said contact is performed in vitro.

3. The method of claim 1 wherein said (PTBR) is human.

4. The method of claim 1 wherein said agonist is a native sequence PTBR ligand or a fragment or subunit thereof.

5. The method of claim 1 wherein said agonist is a small molecule.

6. The method of claim 5 wherein said small molecule is an organic compound.

7. The method of claim 5 wherein said organic compound is selected from the group consisting of benzodiazepines, isoquinoline carboxamides, imidazopyridines, 2-aryl-3-indoleacetamides, and pyrolobenzoxazepines.

8. The method of claim 7 wherein said agonist is Ro5-4864.

9. A method for partial or complete inhibition of a hypertrophic response of cardiac myocytes which comprises contacting said myocytes with an effective amount of an antagonist of a peripheral-type benzodiazepine receptor (PTBR).

10. The method of claim 9 wherein said contact is performed in vitro.

11. The method of claim 9 wherein said PTBR is human.

12. The method of claim 9 wherein said antagonist is a native sequence PTBR ligand or a fragment or subunit thereof.

13. The method of claim 9 wherein said antagonist is a small molecule.

14. The method of claim 13 wherein said small molecule is an organic compound.

15. The method of claim 14 wherein said organic compound is selected from the group consisting of benzodiazepines, isoquinoline carboxamides, imidazopyridines, 2-aryl-3-indoleacetamides, and pyrolobenzoxazepines.

16. The method of claim 15 wherein said antagonist is 1-(2-chlorophenyl)-N-methyl-(1-methylpropyl)-3-isoquinoline carboxamide (PK11195).

17. A method for the treatment of cardiac hypertrophy which comprises administering to a patient an effective amount of an antagonist of a peripheral-type benzodiazepine receptor (PTBR).

18. The method of claim 17 wherein said patient is a mammal.

19. The method of claim 18 wherein said patient is human.

20. The method of claim 19 wherein said antagonist is 1-(2-chlorophenyl)-N-methyl-(1-methylpropyl)-3-isoquinoline carboxamide (PK11195).

21. A method for inducing compensated cardiac hypertrophy which comprises administering to a patient whose heart is subjected to an increased workload, an effective amount of an agonist of a peripheral-type benzodiazepine receptor (PTBR).

22. The method of claim 21 wherein patient is human.

23. The method of claim 22 wherein said agonist is Ro5-4864.

24. A method for augmenting the contractile function of the heart comprising administering to a patient in need an effective amount of an agonist of a peripheral-type benzodiazepine receptor (PTBR).

25. The method of claim 24 wherein said patient is in need of increased blood flow or increased cardiac output.

26. The method of claim 25 wherein said blood flow is peripheral.

27. The method of claim 24 wherein said patient has been diagnosed with ischemia.

28. The method of claim 26 wherein said ischemia is peripheral ischemia.

29. The method of claim 24 wherein the heart of said patient has been injured or has been functionally compromised.

30. The method of claim 24 wherein said patient is need of improved cardiac performance as a result of increased demand for physical exercise.

31. The method of claim 30 wherein said patient has a disability or an atrio-ventricular (A-V) shunt.

32. A method of screening for an antagonist of a peripheral-type benzodiazepine receptor (PTBR) which comprises contacting a cardiac myocyte of hypertrophic phenotype with a candidate molecule and monitoring a reduction in hypertrophy.

33. A method for the prevention of decompensated cardiac hypertrophy which comprises administering to a patient an effective amount of an antagonist of a peripheral-type benzodiazepine receptor (PTBR).

34. A method for the treatment of heart failure comprising administering to a patient an effective amount of an antagonist of a peripheral-type benzodiazepine receptor (PTBR).

35. The method of claim 34 wherein said treatment is the prevention of heart failure.

36. The method of claim 35 wherein said heart failure is congestive heart failure.

37. A method for the treatment of a patient initially in need of increased blood flow, but subsequently developing or at risk of developing decompensated cardiac hypertrophy, comprising administering to said patient an agonist of a PTBR receptor followed by the administration of an antagonist of a PTBR receptor.

* * * * *